United States Patent
Howard

(10) Patent No.: US 11,004,461 B2
(45) Date of Patent: May 11, 2021

(54) REAL-TIME VOCAL FEATURES EXTRACTION FOR AUTOMATED EMOTIONAL OR MENTAL STATE ASSESSMENT

(71) Applicant: Newton Howard, Providence, RI (US)

(72) Inventor: Newton Howard, Providence, RI (US)

(*) Notice: Subject to any disclaimer, the term of this patent is extended or adjusted under 35 U.S.C. 154(b) by 0 days.

(21) Appl. No.: 16/105,301

(22) Filed: Aug. 20, 2018

(65) Prior Publication Data
US 2019/0074028 A1    Mar. 7, 2019

Related U.S. Application Data

(60) Provisional application No. 62/553,137, filed on Sep. 1, 2017.

(51) Int. Cl.
*G10L 25/63* (2013.01)
*G10L 25/87* (2013.01)
(Continued)

(52) U.S. Cl.
CPC .......... *G10L 25/63* (2013.01); *G06N 3/0427* (2013.01); *G06N 3/0445* (2013.01); *G06N 3/084* (2013.01);
(Continued)

(58) Field of Classification Search
CPC ......... G10L 25/63; G10L 25/00; G10L 25/03; G10L 25/27; G10L 25/45; G10L 25/51;
(Continued)

(56) References Cited

U.S. PATENT DOCUMENTS

| | | | |
|---|---|---|---|
| 2013/0166291 A1* | 6/2013 | Lech | G10L 17/26 704/232 |
| 2016/0078771 A1* | 3/2016 | Zhuang | G10L 15/26 434/236 |

(Continued)

OTHER PUBLICATIONS

L.R. Rabiner and R.W. Schafer, Digital Processing of Speech Signals, Prentice Hall, Englewood Cliffs, NJ, 1979.
(Continued)

*Primary Examiner* — Qi Han
(74) *Attorney, Agent, or Firm* — Smith, Gambrell & Russell, LLP

(57) ABSTRACT

Embodiments of the present systems and methods may provide techniques for extracting vocal features from voice signals to determine an emotional or mental state of one or more persons, such as to determine a risk of suicide and other mental health issues. For example, as a person's mental state may indirectly alters his or her speech, suicidal risk in, for example, hotline calls, may be determined through speech analysis. In embodiments, such techniques may include preprocessing of the original recording, vocal feature extraction, and prediction processing. For example, in an embodiment, a computer-implemented method of determining an emotional or mental state of a person, the method comprising acquiring an audio signal relating to a conversation including the person, extracting signal components relating to an emotional or mental state of at least the person, and outputting information characterizing the extracted emotional or mental state of the person.

18 Claims, 28 Drawing Sheets

(51) Int. Cl.

| | |
|---|---|
| *G10L 15/20* | (2006.01) |
| *G06N 7/00* | (2006.01) |
| *G10L 25/21* | (2013.01) |
| *G10L 25/27* | (2013.01) |
| *G10L 25/18* | (2013.01) |
| *G16H 50/20* | (2018.01) |
| *G06N 3/04* | (2006.01) |
| *G16H 50/30* | (2018.01) |
| *G06Q 50/22* | (2018.01) |
| *G06N 3/08* | (2006.01) |
| *G10L 25/24* | (2013.01) |
| *G06N 5/00* | (2006.01) |
| *G10L 25/78* | (2013.01) |
| *G10L 15/16* | (2006.01) |

(52) U.S. Cl.
CPC ............... *G06N 7/00* (2013.01); *G06Q 50/22* (2013.01); *G10L 15/20* (2013.01); *G10L 25/18* (2013.01); *G10L 25/21* (2013.01); *G10L 25/27* (2013.01); *G10L 25/87* (2013.01); *G16H 50/20* (2018.01); *G16H 50/30* (2018.01); *G06N 5/003* (2013.01); *G06N 7/005* (2013.01); *G10L 15/16* (2013.01); *G10L 25/24* (2013.01); *G10L 25/78* (2013.01); *G10L 2025/783* (2013.01)

(58) Field of Classification Search
CPC ......... G10L 25/66; G10L 25/75; G10L 25/78; G10L 25/84
USPC ....... 704/270, 272, 1, 9, 231, 233, 236, 243, 704/250, 251, 255, 257
See application file for complete search history.

(56) References Cited

U.S. PATENT DOCUMENTS

2018/0214061 A1* 8/2018 Knoth ..................... A61B 5/165
2018/0366117 A1* 12/2018 Carreras ................. G10L 15/20

OTHER PUBLICATIONS

M. P. Norton and D. G. Karczub, Fundamentals of Noise and Vibration Analysis for Engineers, Cambridge University Press, Cambridge, UK, 2003.
Karel Dudacek, Short Time Delay Measurement, University of West Bohemia in Pilsen, Jul. 2015.
E.W. Weisstein, Cross-Correlation, Wolfram MathWorld, https://mathworld.wolfram.com/Cross-Correlation.html.
E.W. Weisstein, Cross-Correlation Theorem, Wolfram MathWorld, https://mathworld.wolfram.com/Cross-CorrelationTheorem.html.
F.H. Thanoon, Robust Regression by Least Absolute Deviations Method, International Journal of Statistics and Applications, 2015.
T. Hastie, R. Tibshirani, J. Friedman, The Elements of Statistical Learning: Data Mining, Inference, and Prediction, Springer, 2009.
M. Senior, Phase Demystified: Understanding Phase Cancellation, Sound On Sound, Apr. 2008.
Audacity team, Invert, Audacity Manual, https://manual.audacityteam.org/man/invert.html, Mar. 2017.
F.G. Germain, D.L. Sun and G.J. Mysore, Speaker and Noise Independent Voice Activity Detection, Mar. 2013.
K. Sakhnov, E. Verteletskaya and B. Simak, Approach for Energy-Based Voice Detector with Adaptive Scaling Factor, International Journal of Computer Science, Nov. 2009.
J. Kola, C. Espy-Wilson, and T. Pruthi, Voice Activity Detection, Merit Bien, 2011.
J. Ramirez, J.M. Gorriz and J.C. Segura, Voice Activity Detection. Fundamentals and Speech Recognition System Robustness, Robust Speech Recognition and Understanding, Jun. 2007.
D. Vlaj, M. Kos and Z. Kacic, Quick and efficient definition of hangbefore and hangover criteria for voice activity detection, International Conference on Systems, Signals and Image Processing, Jul. 2016.
R.A. Dobie, S. Van Hemel, Basics of Sound, the Ear, and Hearing, Hearing Loss: Determining Eligibility for Social Security Benefits, 2004.
F.J. Harris, On the Use of Windows for Harmonic Analysis with the Discret Fourier Transform, Proceedings of the IEEE, vol. 66, 1978.
S.B. Davis and P. Mermelstein, Comparison of parametric representations for monosyllabic word recognition in continuously spoken sentences, Acoustics, Speech and Signal processing, IEEE Transactions on, 1980.
J. Krajewski, R. Wieland, D. Sommer and M. Golz, A speech adapted pattern recognition framework for measuring energetic states using low level descriptors and functionals, Proceedings of Measuring Behavior, Aug. 2008.
T. Ganchev, N. Fakotakis and G. Kokkinakis, Comparative evaluation of various MFCC implementations on the speaker verification task, Jan. 2005.
N. Lulla and N. Purohit, An improved algorithm for efficient computation of MFCC, India Conference (INDICON), Dec. 2014.
S. Lalitha, D. Geyasruti, R. Narayanan and Shravani M, Emotion Detection Using MFCC and Cepstrum Features, Procedia Computer Science, 2015.
J.S. Devi, S. Yarramalle and S.P. Nandyala, Speaker Emotion Recognition Based on Speech Features and Classification Techniques, I.J. Computer Network and Information Security, Jul. 2014.
J. Lyons, Mel Frequency Cepstral Coefficient (MFCC) tutorial, Practical Cryptography, 2009-2012.
H. Fayek, Speech Processing for Machine Learning: Filter banks, Mel-Frequency Cepstral Coefficients (MFCCs) and What's In-Between, Apr. 2016.
L.R. Rabiner, A tutorial on hidden Markov models and selected applications in speech recognition, Proceedings of the IEEE, Feb. 1989.
J. Stadermann, G. Rigoll, Hybrid NN/HMM Acoustic Modeling Techniques for Distributed Speech Recognition, Speech Communication, Aug. 2006.
S. Hochreiter and J. Schmidhuber, Long Short-term Memory, Neural Computation, Dec. 1997.
A. Graves and J. Schmidhuber, Framewise phoneme classification with bidirectional LSTM networks, Neural Networks, Aug. 2005.
M. Schuster and K.K. Paliwal, Bidirectional Recurrent Neural Networks,IEEE Transactions on Signal Processing, 1997.
A. Graves, A.R. Mohamed and G. Hinton, Speech recognition with deep recurrent neural networks, Acoustics, Speech and Signal Processing (ICASSP), May 2013.
H. Sak, A. Senior, F. Beaufays, Long Short-Term Memory Based Recurrent Neural Network Architectures for Large Vocabulary Speech Recognition, Google, Feb. 2014.
M. Rubashkin and M. Mollison, TensorFlow RNN Tutorial, Silicon Vally Data Science, https://www.svds.com/tensorflow-rnn-tutorial/, Mar. 2017.
H. Sak, A. Senior, K. Rao and F. Beaufays, Fast and Accurate Recurrent Neural Network Acoustic Models for Speech Recognition, Google, Jul. 2015.
A. Graves, S. Fernandez, F. Gomez and J. Schmidhuber, Connectionist Temporal Classification: Labelling Unsegmented Sequence Data with Recurrent Neural Networks, IDSIA, Jun. 2006.
C. Veaux, J. Yamagishi and K. MacDonald, CSTR VCTK Corpus: English Multi-speaker Corpus for CSTR Voice Cloning Toolkit, University of Edinburgh, 2016.
V. Panayotov, G. Chen, D. Povey and S. Khudanpur, LibriSpeech ASR corpus, The Johns Hopkins University, Apr. 2015.
Philippe Rémy, Tensorflow CTC Speech Recognition, GitHub, https://github.com/philipperemy/tensorflow-ctc-speech-recognition, Apr.-Aug. 2017.
J. Lyons, Python Speech Features library, https://github.com/jameslyons/python_speech_features, 2013.
P. Boersma and D. Weenink, Praat: doing phonetics by computer, Version 5.3.51, https://www.fon.hum.uva.nl/praat/, Jun. 2013.

(56) References Cited

OTHER PUBLICATIONS

B. Mathieu, S. Essid, T. Fillon, J. Prado, G. Richard, YAAFE, an Easy to Use and Efficient Audio Feature Extraction Software, Affective Computing and Intelligent Interaction and Workshops, Dec. 2009.

S. Saleem, M. Pacula, R. Chasin, R. Kumar, R. Prasad, M. Crystal, B. Marx, D. Sloan, J. Vasterling and T. Speroff, Automatic detection of psychological distress indicators in online forum posts, A Signal and Information Processing Association Annual Summit and Conference (APSIPA ASC), Dec. 2012.

PortAudio community, PortAudio: Portable Cross-platform Audio I/O, retrieved from http://www.portaudio.com/, 2011.

A. Rousseau, P. Deléglise, Y. Esteve, TED-LIUM: an Automatic Speech Recognition dedicated corpus, Laboratoire Informatique de l'Université du Maine, May 2012.

W.M. Fisher, G.R. Doddington, K.M. Goudie-Marshall, C. Jankowski, A. Kalyanswamy, S. Basson and J. Spitz, NTIMIT LDC93S2, Philadelphia: Linguistic Data Consortium, https://catalog.ldc.upenn.edu/LDC93S2, 1993.

R. Vergin and D. O'Shaughnessy, Pre-Emphasis and Speech Recognition, Electrical and Computer Engineering, Sep. 1995.

F. Eyben, Real-time Speech and Music Classification by Large Audio Feature Space Extraction, Springer Theses, Recognizing Outstanding Ph.D. Research, 2016.

Google brain team, TensorFlow web page, Google, Nov. 2015.

Google Research, TensorFlow: Large-Scale Machine Learning on Heterogeneous Distributed Systems, White page, Nov. 2015.

S. Abrahams, D. Hafner, E Erwitt and A. Scarpinelli, TensorFlow for Machine Intelligence: A hands-on introduction to learning algorithms, Bleeding edge press, May 2016.

N. Cummins, S. Scherer, J. Krajewski, S. Schnieder, J. Epps and T.F. Quatieri, A review of depression and suicide risk assessment using speech analysis, Speech communication, Jul. 2015.

World Health Organization, Preventing suicide: A global imperative, World Health Organization, 2014.

M. Valstar, B. Schuller, K. Smith, T. Almaev, F. Eyben, J. Krajewski, R. Cowie and M. Pantic, AVEC 2014—3D Dimensional Affect and Depression Recognition Challenge, AVEC 2014, Nov. 2014.

J.R. Williamson, T.F. Quatieri, B.S. Helfer, G. Ciccarelli, D.D. Mehta, Vocal and Facial Biomarkers of Depression based on Motor Incoordination and Timing, AVEC 2014, Nov. 2014.

L. He, D. Jiang, L. Yang, E. Pei, P. Wu and H. Sahli, Multimodal Affective Dimension Prediction Using Deep Bidirectional Long Short-Term Memory Recurrent Neural Networks, AVEC 2015, Oct. 2015.

L. Yang, D. Jiang, L. He, E. Pei, M.C. Oveneke and H. Sahli, Decision Tree Based Depression Classification from Audio Video and Language Information, AVEC 2016, Oct. 2016.

B. Schuller, S. Steidl and A. Batliner, The INTERSPEECH 2009 Emotion Challenge, INTERSPEECH 2009, Jan. 2009.

B. Schuller, S. Steidl, A. Batliner, F. Burkhardt, L. Devillers, C. Muüller and S. Narayanan, The INTERSPEECH 2010 Paralinguistic Challenge, INTERSPEECH 2010, Jan. 2010.

B. Schuller, S. Steidl, A. Batliner, E. Nöth, A. Vinciarelli, F. Burkhardt, R. van Son, F. Weninger1, F. Eyben1, T. Bocklet, G. Mohammadi and B. Weiss, The INTERSPEECH 2012 Speaker Trait Challenge, INTERSPEECH 2012, Jan. 2012.

B. Schuller, S. Steidl, A. Batliner, A. Vinciarelli, K. Scherer, F. Ringeval, M. Chetouani, F. Weninger, F. Eyben, E. Marchi, M. Mortillaro, H. Salamin, A. Polychroniou, F. Valente and S. Kim, The INTERSPEECH 2013 Computational Paralinguistics Challenge: Social Signals, Conflict, Emotion, Autism, INTERSPEECH 2013, Jan. 2013.

B. Schuller, S. Steidl, A. Batliner, J. Hirschberg, J.K. Burgoon, A. Baird, A. Elkins, Y. Zhang, E. Coutinho and K. Evanini, The INTERSPEECH 2016 Computational Paralinguistics Challenge: Deception, Sincerity and Native Language, INTERSPEECH 2016, Sep. 2016.

O. Lartillot and P. Toiviainen, A MATLAB Toolbox for Musical Feature Extraction from Audio, Conference on Digital Audio Effects, Sep. 2007.

B. Mathieu, S. Essid, T. Fillon, J. Prado and G. Richard, YAAFE, an Easy to Use and Efficient Audio Feature Extraction Software, Institute Telecom Paris, Jan. 2010.

F. Eyben, M. Wöllner and B. Schuller, openSMILE—The Munich Versatile and Fast Open-Source Audio Feature Extractor, ACM International Conference on Multimedia, Jan. 2010.

S. Vaishnav and S. Mitra, Speech Emotion Recognition: A Review, International Research Journal of Engineering and Technology, Apr. 2016.

P. Shen, Z. Changjun, X. Chen, Automatic Speech Emotion Recognition Using Support Vector Machine, International Conference on Electronic and Mechanical Engineering and Information Technology, Aug. 2011.

H.M. Fayek, M. Lech and L. Cavedon, Towards Real-time Speech Emotion Recognition using Deep Neural Networks, Signal Processing and Communication Systems (ICSPCS), Dec. 2015.

A. Rajeswari, P. Sowmbika and P. Kalaimagal, Improved emotional speech recognition algorithms, Wireless Communications, Signal Processing and Networking (WiSPNET), Mar. 2016.

S. Mirsamadi, E. Barsoum and C. Zhang, Automatic speech emotion recognition using recurrent neural networks with local attention, Acoustics, Speech and Signal Processing (ICASSP), Mar. 2017.

M. Pacula, T. Meltzer, M. Crystal, A. Srivastava and B. Marx, Automatic detection of psychological distress indicators and severity assessment in crisis hotline conversations, Acoustics, Speech and Signal Processing (ICASSP), May 2014.

Victor Volkman, PortAudio: Portable Audio Processing for All Platforms, developer.com, Mar. 2006, retrieved from https://www.developer.com/net/cplus/article.php/3590641/PortAudio-Portable-Audio-Processing-for-All-Plafforms.htm.

Hubert Pham, PyAudio, 2006, retrieved from https://people.csail.mit.edu/hubert/pyaudio/.

Hugh Robjohns, Processing Stereo Audio Files, Sound On Sound, Nov. 2010.

Eric Tarr, Learn computer programming and audio engineering, Hack Audio, 2016, https://www.hackaudio.com/.

IBM Corporation and Microsoft Corporation, Multimedia Programming Interface and Data Specifications 1.0, Aug. 1991.

Microsoft Hardware Dev Center, Multiple channel audio data and WAVE files, Mar. 2007.

\* cited by examiner

Fig. 25

Original validation text: the rainbow is a division of white light into many beautiful colors
Decoded validation text: the rainbow is a divtio of white ligh into many e autigful coolors

REAL-TIME VOCAL FEATURES EXTRACTION FOR AUTOMATED EMOTIONAL OR MENTAL STATE ASSESSMENT

CROSS-REFERENCE TO RELATED APPLICATIONS

This application claims the benefit of U.S. Provisional Application No. 62/553,137, filed Sep. 1, 2017, the contents of which are hereby incorporated by reference herein in their entirety.

BACKGROUND

The present invention relates to techniques for extracting vocal features from voice signals to determine an emotional or mental state of one or more persons, such as to determine a risk of suicide and other mental health issues.

Mental health disorders, and more particularly depression and suicide, have become a major concern for society. Conventional diagnosis suffers from a lack of accuracy and reliability due to patient self-reporting, Overall, mental health disorders are under-diagnosed and under-treated. Public health interventions often include strategies, such as the suicide crisis hotline. However, the counselors answering the calls are not necessarily mental health professionals and can overtook subtle signs. The human voice carries much more than simply the linguistic content. Paralinguistic content, including information regarding emotions, is also present. As a person's mental state indirectly alters his or her speech, a person's mental state may be reflected in the paralinguistic content of their speech.

Accordingly, a need arises for techniques for extracting vocal features from voice signals to determine an emotional state or mental of one or more persons, such as to determine a risk of suicide and other mental health issues.

SUMMARY

Embodiments of the present systems and methods may provide techniques for extracting vocal features from voice signals to determine an emotional or mental state of one or more persons, such as to determine a risk of suicide and other mental health issues. For example, as a person's mental state may indirectly alters his or her speech, suicidal risk in, for example, hotline calls, may be determined through speech analysis. Such techniques may provide real-time feedback regarding the caller's suicidal impulse and the counselor's apprehension level. In embodiments, such techniques may include preprocessing of the original recording, vocal feature extraction, and prediction processing.

For example, in an embodiment, a computer-implemented method of determining an emotional or mental state of a person, the method comprising acquiring an audio signal relating to a conversation including the person, extracting signal components relating to an emotional or mental state of at least the person, and outputting information characterizing the extracted emotional or mental state of the person.

In embodiments, acquiring the audio signal relating to a conversation may comprise recording a conversation between a caller to suicide help line and a counselor of the suicide help line. The signal components relating to emotional intent of at least one party may comprise extracting signal features from the audio signal comprising discriminative speech indicators, which differentiate between speech and silence, determining which extracted signal features to use, and enhancing the robustness of the determination against background noise. Determining which extracted signal features to use may comprise using at least one of a linear classifier model, a decision tree model, a Gaussian mixture model, a Neural Network model, a thresholding model and enhancing the robustness of the determination comprises using a hysteresis rule. The at least one model may be trained using recordings of conversations wherein the emotional or mental state of the at least one party to the conversation has been previously determined. Extracting signal features from the audio signal may comprise using at least one of: an Energy, Zero-crossing rate method, a linear prediction and pitch estimation method, a Spectral entropy method, a Spectral envelope method, and a Cepstral Coefficient method. Extracting signal features from the audio signal may comprise performing pre-emphasis filtering on the audio signal to generate a pre-emphasis filtered signal, performing windowing processing on the pre-emphasis filtered signal to generate a windowed signal, performing discrete Fourier transform processing on the windowed signal to form a Fourier transformed signal, performing power spectrum processing on the Fourier transformed signal to form a power spectrum signal, performing Mel-Cepstral filter bank processing on the power spectrum signal to form a Mel-Cepstral filter bank signal, performing logarithm processing on the Mel-Cepstral filter bank signal to form a logarithm signal, performing discrete cosine transform processing on the logarithm signal to form a discrete cosine transformed signal, performing sinusoidal littering processing on the discrete cosine transformed signal to form a plurality of Mel-Cepstral coefficients, performing discrete energy spectrum processing on the power spectrum signal to form an energy spectrum signal, performing logarithm processing on the energy spectrum signal to form an energy coefficient, and performing delta processing on the plurality of Mel-Cepstral coefficients and on the energy coefficient to form a plurality of Mel-Cepstral coefficients deltas and double deltas and an energy coefficient delta and double delta.

In an embodiment, a system for intent extraction may comprise a processor, memory accessible by the processor, and computer program instructions stored in the memory and executable by the processor to perform acquiring an audio signal relating to a conversation including the person, extracting signal components relating to an emotional or mental state of at least the person, and outputting information characterizing the extracted emotional or mental state of the person.

In an embodiment, a computer program product for intent extraction may comprise a non-transitory computer readable storage having program instructions embodied therewith, the program instructions executable by a computer, to cause the computer to perform a method comprising acquiring an audio signal relating to a conversation including the person, extracting signal components relating to an emotional or mental state of at least the person, and outputting information characterizing the extracted emotional or mental state of the person.

BRIEF DESCRIPTION OF THE DRAWINGS

The details of the present invention, both as to its structure and operation, can best be understood by referring to the accompanying drawings, in which like reference numbers and designations refer to like elements.

FIG. 25 is an exemplary illustration of a network transcription according to embodiments of the present systems and methods.

DETAILED DESCRIPTION

Figure 1:
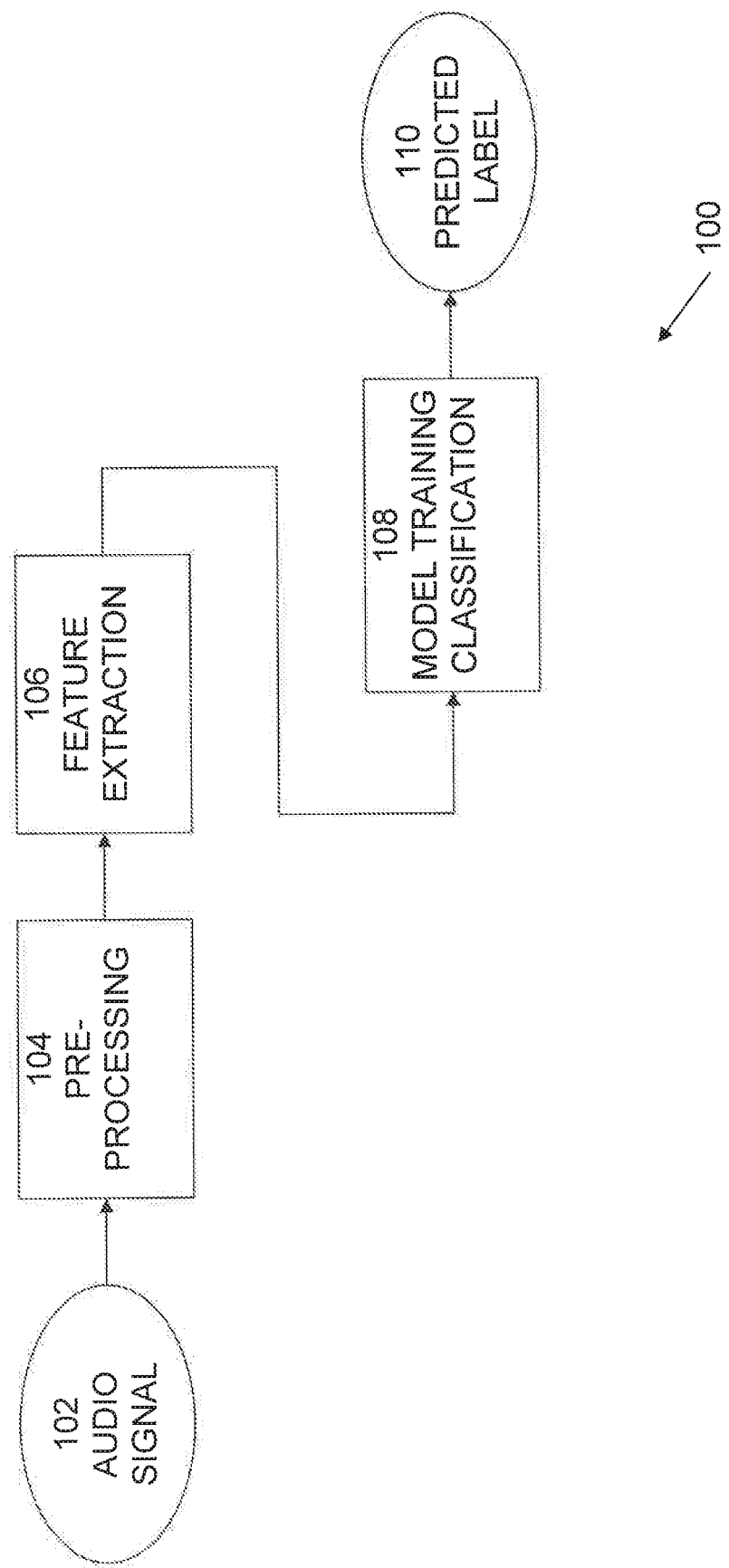
FIG. 1 illustrates an exemplary speech analysis system in which embodiments of the present systems and methods may be implemented.

Embodiments of the present systems and methods may provide techniques for extracting vocal features from voice signals to determine an emotional or mental state of one or more persons, such as to determine a risk of suicide and other mental health issues. Embodiments of the present systems and methods may be applicable to determining any type of emotional or mental state of one or more persons. The determination of risk of suicide based on a call to a suicide hotline is one example of an application of the present systems and methods. However, the present systems and methods are not limited to application to this example. Rather, embodiments of the present systems and methods may be applicable to determining any type of emotional or mental state of one or more persons.

Regarding the example of determining risk of suicide, as a person's mental state may indirectly alter his or her speech, suicidal risk in, for example, hotline calls, may be determined through speech analysis. Such techniques may provide real-time feedback regarding the caller's suicidal impulse and the counselor's apprehension level. In embodiments, such techniques may include preprocessing of the original recording, vocal feature extraction, and prediction processing.

Psychological or mental health disorders represent growing risks and concerns for society. About one in four individuals suffers from such problems at some point during their lifetime. Mental health disorders principally affect a person's interpersonal relationships, as well as social and educational life. On a larger scale, mental health disorders can burden social, justice and economic systems.

Today, one of the main mental health concerns is related to depression and suicide. According to World Health Organization, the worldwide number of persons suffering from depression exceeds 300 million. Research studies have shown that there are significant correlations between suicide and depression, with evidence that over 90% of suicide situations are linked to mental health problems and more specifically depression. Those dramatic numbers reinforce the necessity to act and find a solution.

Every year about 800,000 individuals lose their lives due to suicide, and even more attempt it. Research shows that for one suicide, there are more than 20 attempts. And the worrisome problem is the increasing rate, with 60% more cases in the last 45 years, Nowadays, suicide accounts for 1.4% of worldwide deaths. However, suicide, if recognized early enough, is preventable.

The conventional way to detect mental health disorders, such as depression, is done mostly by clinical interview. The Hamilton Rating Scale for Depression and the Suicide Probability Scale are just some examples. Besides being a costly and time-consuming process, the main problem with such measures is the lack of accuracy and reliability due to their reliance on patient self-reporting, as well as the lack of attention put on observable behavior. These diagnostics can be strongly biased by subjective observation and the absence of real-time or more natural assessments. The unpredictability of suicidal behavior makes diagnosis even more complicated. All of this results in under-diagnosed and under-treated disorders.

Even with pharmacotherapy and psychotherapy playing an essential role in the treatment of such disorders, a large number of suicides still occur. As a complementary tool, public health interventions also have value in treating such behavior. Prevention is a part of universal strategies that target the whole population and try to stop the onset. But there are also programs that address high-risk individuals in particular. One of these is the suicide crisis hotline. Such hotlines can be considered as last means to get help for individuals that might attempt suicide. Typically, such services are free and easily-available. Such accessible help has proven to significantly decrease negative outcomes. However, counsellors are not necessarily mental health professionals with significant clinical experience. Therefore, complex and subtle signs might be overlooked or not considered by the phone counsellor. Recently developed innovative techniques might improve the success rate of such strategies.

Hotline speech analysis. Depression and emotions are inherently associated. Some robust correlations have been found between the behavior of depressed persons and the three affective dimensions, which are arousal, dominance and valence. However, it remains relatively difficult to quantitatively evaluate human emotions. Potential biomarkers such as facial expressions, body posture and gesture, muscular activity, body temperature and speech carry relevant information regarding the emotions experienced by an individual, which turns out to reflect his or her mental and emotional state. More precisely, avoiding eye contact, dampened facial expressive responses, communicating only with short sentences, and flat intonation are typical behaviors of abnormal social interactions that might be related to depression. Even though analyzing facial expression and gestures is probably the most accurate method to reveal someone's emotions, with experience, people tend to learn how to control their expressions. Another problem with this approach is that it is only capable of detecting expressions that are considered to be external, like happiness, anger or sadness.

As previously mentioned, mental state also indirectly alters speech and leads to a growing interest in vocal-based features. Speech is one of the principal communication methods between human beings. The voice contains much more information than simply linguistic content such as words or sentences. It also consists of paralinguistic content, like affect, mood and speaker states. Paralinguistic information carried in speech can help identify the mental or emotional state of speakers. Looking at a more technical point of view, voice can be defined as an acoustic signal, which is physically characterized by small air pressure modulations. Those variations are then ultimately transformed into digital signal. Signal processing methods can be applied to the audio sample in order to extract desired information relative to speech. Thus, different speech characteristics and vocal parameters are expressed for each emotion felt. Typically, monotony, slowness, slurring, hoarseness and atypical breathing are observable depression-related signs.

In embodiments, solutions regarding mental health problems may include tools that are capable of automatically evaluating a voice signal, such as in call to a suicide hotline, to determine suicidal risk through speech analysis. Embodiments may provide real-time feedback to counsellors and rapid situation assessment to help the decision making process.

Persons who are in emotional distress commonly call hotline services, looking for help or simply someone to listen. In embodiments, a counsellor may answer the phone while switching on the analysis tools. Using an input sample, which may be as small as possible in order to keep up with the real time analysis requirement, a severity index related to the caller's suicidal impulse may be output, as well as feedback regarding the counsellor's apprehension level. Typically, such signals contain high levels of background noise because of the real-time nature of the problem. The quality of the listening device and external conditions also contribute to the elevated noise level. Those important aspects need to be considered during the development of the system.

An example of a typical speech analysis system 100 is shown in FIG. 1. System 100 may include an audio signal source 102, pre-processing 104, feature extraction 106, model training and classification 108, and predicted label output 110. Audio signal source 102 may be, for example, audio recordings from hotline crisis calls. Due to the typical signal characteristics of such inputs, adjustments and corrections of the signal may be performed by pre-processing 104. To analyses and generate feedback from both voices, the individual in crisis and the counsellor, pre-processing 104 may include the separation of the two speaker voices, as well as the corrections needed for its implementation, namely time delay and gain difference between the two recorded channels, Pre-emphasis may also be performed here as it is used in nearly all speech analysis systems.

The extracted and corrected audio signal is still not directly fed to the classifier, because a lot of redundant and non-relevant information is present in the sound wave. Feature extraction 106 may extract only those characteristics carrying pertinent information for the purpose of the task. The features that are extracted may be selected in order to achieve efficiency and system performance.

Model training and classification 108 may include training of a classification model using a selected dataset, and later, classification of input audio signals to generate predicted label output 110.

Pre-processing. Recording. In embodiments, the recording and streaming of the line calls may be performed with any audio input/output (I/O) software, such as PORTAUDIO®. Such an audio I/O library may use, for example, a straightforward C or C++ API, developed for the purpose of sound processing. A big advantage of such a library is its flexibility and ability to be compiled on various computer operating systems, such as GNU/Linux, Microsoft Windows, and Apple Mac OS X.

Stereo to mono. In embodiments, the line calls may be receded through software, such as the PYAUDIO® version of PORTAUDIO®, as stereo signals. Stereophonic sound is one of the most common audio recording formats nowadays. All of the currently developed devices try to mimic, as close as possible, what is happening within human hearing, where the sound is perceived in stereo. The slight time difference between sound arrival at the right or left ear is computed by the brain to determine the relative position of the sound source. Engineers can re-create natural hearing and therefore reproduce the illusion of sounds coming from multiple directions. Stereographic projection is thus used to generate the perception of localized sound. This phenomena can be achieved by using several audio channels (two-channel stereo is the most common format). The microphones are placed at different locations and are activated at the same time. The recording of each channel will show slight variations in sound-pressure-level and time-of-arrival, which are similar to natural hearing and used to localize the recorded signal.

Now, in order to be able to split the recording into individual mono signals, it is important to consider how the information is stored and organized within the stereo signal, Looking at a more technical and physical aspect of the human voice, this acoustic signal can be characterized as small variations in air pressure. During recording, those pressure modulations are converted into an electric current through the vibrations of the microphone membrane. For processing, this analogue signal needs to be discretized (in amplitude and time), which results in a digital signal.

Figure 2:
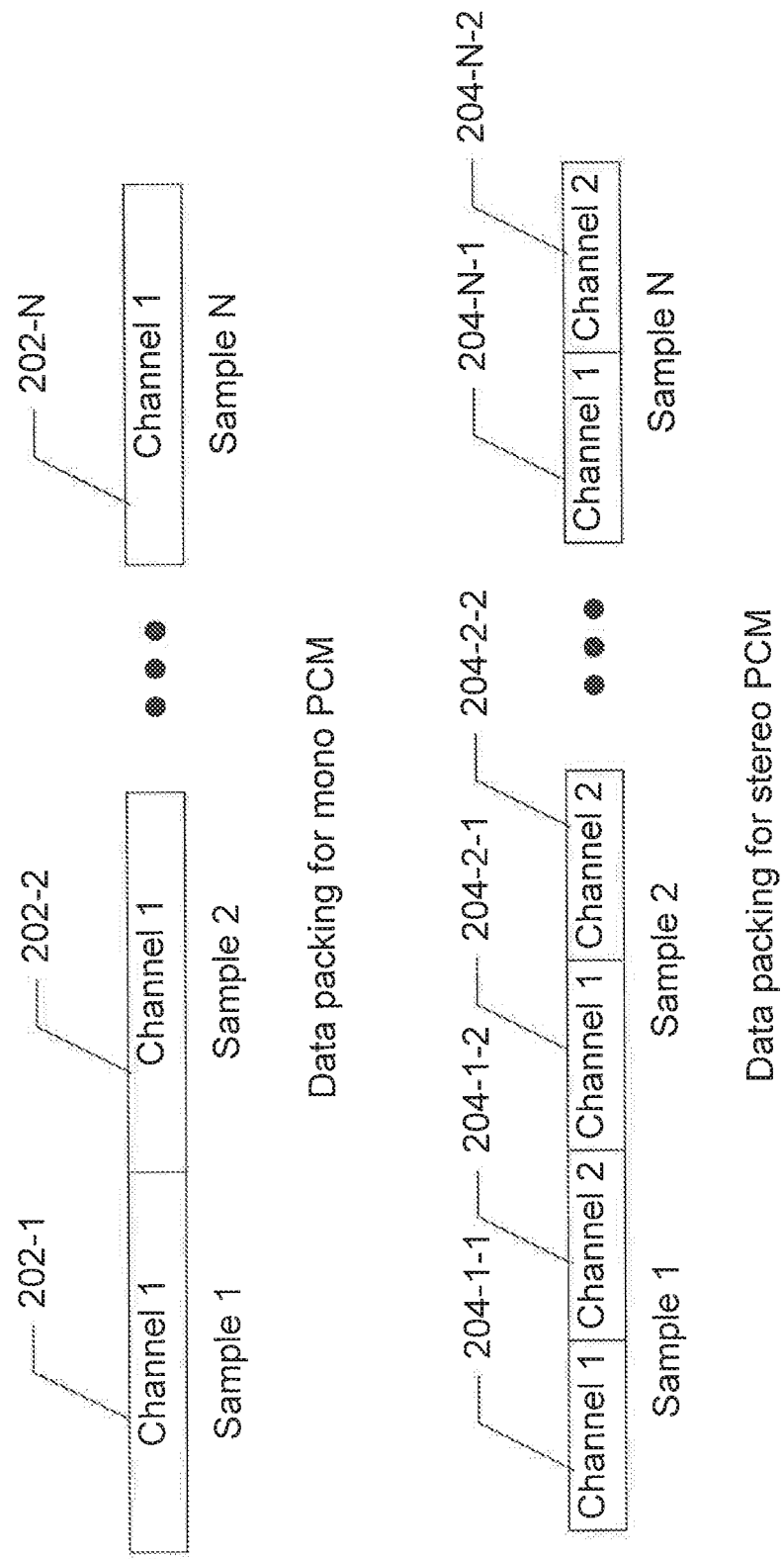
FIG. 2 is an exemplary data diagram of a Pulse Code Modulation format of digital audio according to embodiments of the present systems and methods.

A standard format of digital audio is Pulse Code Modulation (PCM). As shown in FIG. 2, in a single-channel PCM file, the samples 202-1 to 202-N are simply kept successively. In a different manner, samples of each channel are interleaved in a multi-channel file, as illustrated in FIG. 2. In a two-channel stereo signal, the data is stored in the following way: one sample of channel 2 204-1-2 comes after one sample of channel 1 204-1-1 and so on. A sample frame consists of the combination of one sample of each channel at a particular moment in time. Understanding this concept helps to convert the stereophonically recorded signal into two monophonic signals.

In embodiments, after the separation of each channel, one channel may contain only the counsellor's voice, while both the caller's and counsellor's voices may be included in a second channel. In embodiments, each voice may be analyzed individually in order to generate not only a severity index related to the caller's suicidal impulse but also feedback regarding the counsellor's apprehension level. Accordingly, the next major step is the extraction of the caller's voice from the mixed channel. However, as previously noted, the two channels also may be adjusted, correcting the phase shift and the gain difference between the two signals.

Time delay estimation via cross-correlation. Even though the shift between the two tracks is not perceptible to the human ear, in embodiments, the alignment may be adjusted. For example, signal delay offset may be estimated through analysis of the correlation between different signals. The similarity between two channels can be described in terms of the time shift, $\tau$, from the cross-correlation function. It can be visualized as the displacement of one signal relative to another. For example, a cross-correlation function that may be used is:

$$R_{xy}[t] = (x*y)[t] \quad (1)$$
$$= \sum_{n=-\infty}^{\infty} x*[n]y[n+t] = \sum_{n=-\infty}^{\infty} x*[n-t]y[n]$$
$$= x*[-t]*y[t]$$
$$= \mathcal{F}^{-1}\{X*[f]Y[f]\},$$

where $\mathfrak{F}$ corresponds to the Fourier transform and "*" denotes the complex conjugate. In embodiments, the Fourier transform may be computed using the Fast Fourier Transform process, which may provide a decrease of the computational complexity, going from $O(N^2)$ to $O(N \log N)$. From this approach, the time shift may be computed as the value $\tau$ where the cross correlation is at its absolute maximum:

$$\tau = \underset{t}{\mathrm{argmax}}(x*y)[t]. \quad (2)$$

This measure represents the position in time where the signals are best aligned. Once this delay is estimated, the two channels can be adjusted to obtain the synchronized signals.

Gain difference. For the question of gain difference, the idea is that when looking at a segment where the counsellor is the only one speaking, the two signals can be related through a linear combination such as:

channel1−coefficient·channel2=0.  (3)

The coefficient or multiplicative factor may be determined by considering that if this linear combination is zero for the arrays as a whole, it should also be zero for any instant t. By taking the value of each channel at a given time, the coefficient may be obtained with a straightforward computation. However, due to noise in the signals, such a method may not work properly.

In embodiments, an improved method of computing the coefficient may be through a minimization of either the L-2, Equation (4), or L-1 norm, Equation (5). In both equations, $a_i$ corresponds to the $i^{th}$ element of the vector a, with $i \in [1;n]$.

$$\|a\|_2 = \sqrt{\sum_{i=1}^{n}|\alpha_i|^2} \quad (4)$$

$$\|a\|_1 = \sum_{i=1}^{n}|\alpha_i| \quad (5)$$

The L-2 norm method, also known as Ordinary Least Squares (OLS), aims to minimize the sum of the squared deviation between channel1 and coefficient·channel2, see Equation (6).

$$f(\beta) = \|Y - \beta X\|_2 \quad (6)$$

As demonstrated in Equation (6), the desired multiplicative coefficient can be computed by minimizing the L-2 norm of the linear combination of Equation (3).

$$\hat{\beta} = \underset{\beta}{\mathrm{argmin}} f(\beta) \quad (7)$$
$$= \underset{\beta}{\mathrm{argmin}} \|Y - \beta X\|_2$$
$$= (X'X)^{-1}X'Y$$

The OLS is favorable in the case of independent and normally distributed residuals with stable solutions. But if the fundamental assumptions are not met, this approach breaks down. Its main drawback is its sensitivity to outliers. Since the differences are squared, it seems intuitive to consider, that in the presence of outliers, the error will be much greater than expected and the minimization of this model will be heavily weighted by those outliers. Therefore, OLS computation is not really robust and might lead to a biased estimate.

On the other hand, the Least Absolute Deviation (LAD) deals with the L-1 norm, Equation (5). Instead of minimizing the sum of squares residuals, it uses the absolute difference.

$$f(\beta) = \|Y - \beta X\|_1 \quad (8)$$

An estimation of the factor can be computed thanks to Equation (9), where W denotes a diagonal matrix with elements corresponding to $$\frac{1}{|Y_i - \beta X_i|}$$

on the diagonal and 0 otherwise.

$$\begin{aligned}\hat{\beta} &= \underset{\beta}{\operatorname{argmin}} f(\beta) \\ &= \underset{\beta}{\operatorname{argmin}} \|Y - \beta X\|_1 \\ &= (X'WX)^{-1} X'WY\end{aligned} \quad (9)$$

This method seems to be an interesting alternative of the L-2 norm, as it is more resistant to outlier effects. The drawback here relates to instability and possible multiple solutions, which come from the non-existing analytical solution and the possible weak conditioning of the matrix. This means that small changes or perturbations introduced to the data have a large effect on the estimator.

In embodiments, either or both approaches may be implemented here to define the best estimate of the multiplicative factor and thus to compensate the gain difference between the two channels.

Voice extraction. One of the biggest challenges is linked to the extraction of each voice out of the two channels. The first channel contains only the counsellor's voice, while the second channel presents both voices.

Figure 3:
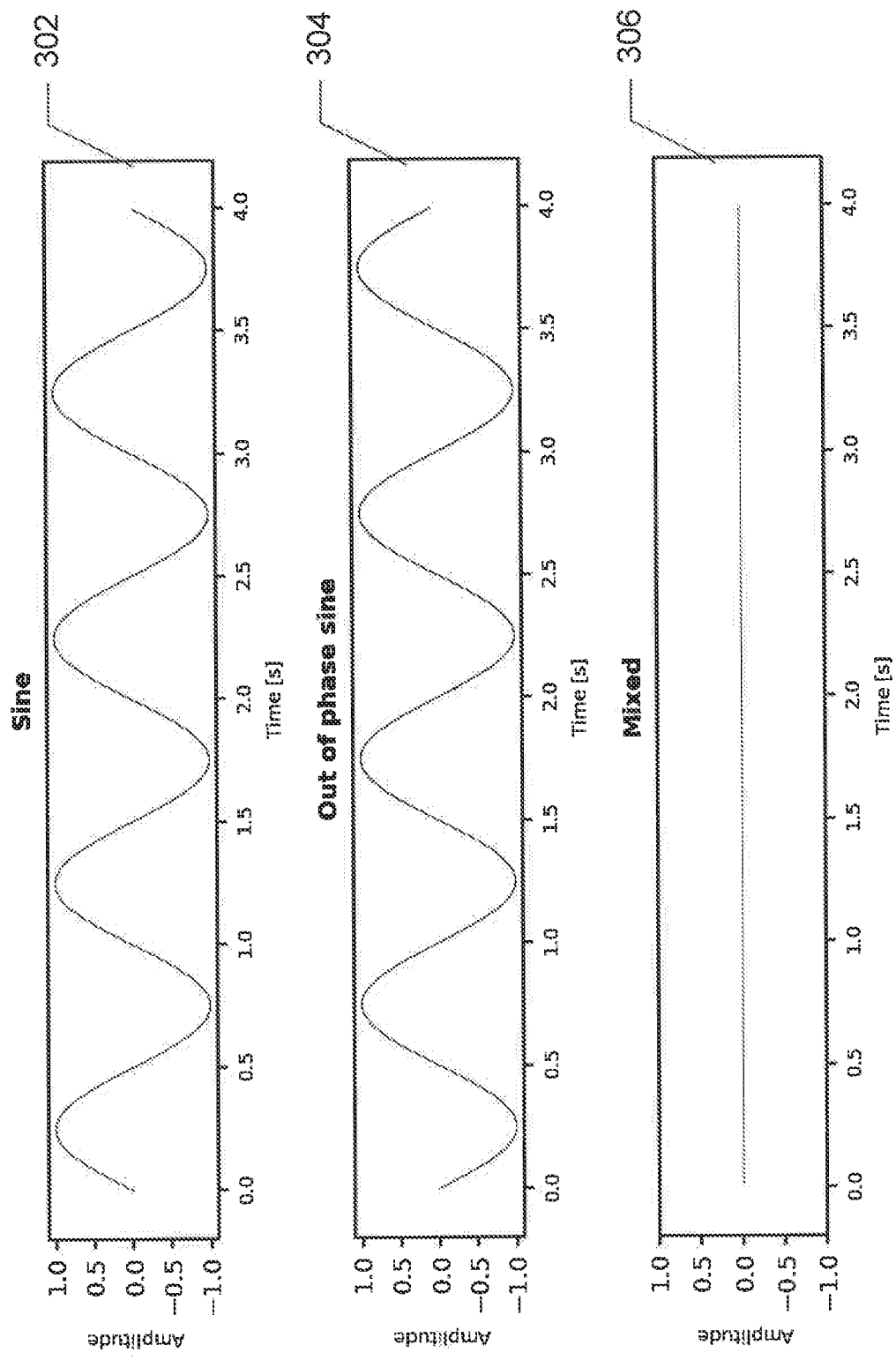
FIG. 3 is an exemplary illustration of phase inversion processing according to embodiments of the present systems and methods.

Phase inversion. In embodiments, this problem may be solved by using phase inversion. Also referred to as phase cancellation or destructive interference, phase inversion is a technical trick commonly used in music remixing to eliminate or extract certain components from a stereo track. The concept simply consists of reversing the polarity of one channel after time and amplitude adjustment. Then mixing a polarity inverted track with another track containing identical audio will suppress the unwanted component. It can mathematically be seen as a subtraction of the signal of one channel to the other. For example, as shown in FIG. 3, sine waves of similar frequency but antagonistic amplitude (signals out of phase), such as sine wave 302 and out of phase sine wave 304, will cancel each other out 306 when properly aligned and combined together.

Detecting the presence of speech within a given noisy audio signal remains a crucial issue in speech processing. To solve this problem, specific algorithms, called Voice Activity Detector (VAD), were developed to identify the active speech periods. It is referred to as a pre-processing step for most speech processing applications, and it is necessary to conduct it accurately. Since relevant information is only present in speech, extracting those particular sequences in the signal can also reduce the amount of data considerably. The property required to qualify an algorithm as a good potential VAD is especially its ability to acquire a constant and satisfying efficiency across various noise levels. Resource-saving, low computational complexity and rapid adjustment are other important aspects to consider.

Figure 4:
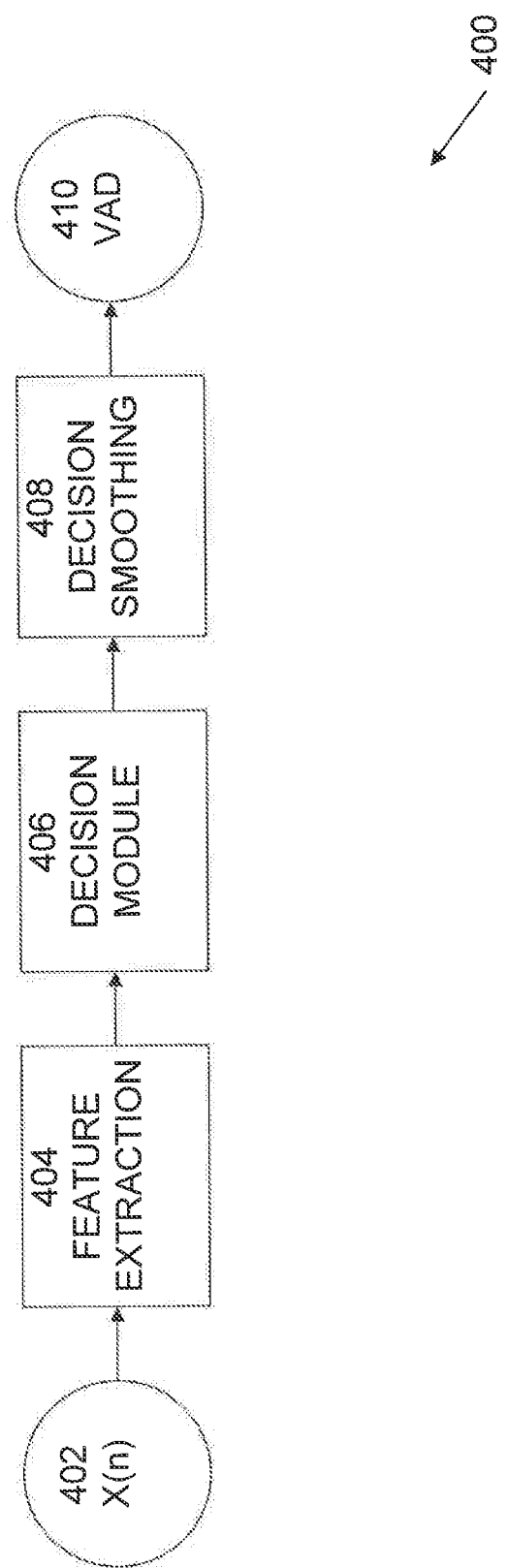
FIG. 4 is an exemplary block diagram of a VAD process and/or system according to embodiments of the present systems and methods.

VAD can be summarized as a feature extraction and discrimination model. The decision to assign a sample to either speech or non-speech category is made based on the feature vector extracted from the audio signal. An example of a VAD process and/or system 400 is shown in FIG. 4. In this example, a signal characterized as X(n) 402 may be input to VAD process and/or system 400.

Signal 402 may be input to feature extraction 404, in which features of the signal may be extracted. The objective of feature extraction is to acquire a set of discriminative speech indicators, which differentiate between speech and silence, Examples of features that may be used in embodiments of VAD algorithms are Energy, Zero-crossing rate, linear prediction and pitch estimation. In embodiments, more advanced methods, such as Spectral entropy, Spectral envelope and Cepstral Coefficients may also be used as VAD features.

The extracted features may be input to decision module 406, which decides which particular extracted features to use. In embodiments, multiple methods with various complexity may be used for to make the decision, which may be equivalent to a classification problem. In embodiments, linear classifier, decision tree, Gaussian Mixture Model and even Neural Network models may be used. In embodiments, the decision rule may be established on a thresholding algorithm. The performance of the VAD depends highly on the decision module and clearly drops as the signal-to-noise-ratio (SNR) decreases, for example, due to increasing background noise. A noise-free signal does not correspond at all to any realistic scenario. The biggest challenge relates to the diverse and fluctuating nature of noise and the human voice. The chosen method mainly depends on the requirements for the desired application.

The output from decision module 406 may be input to decision smoothing 408, which may enhancing the robustness of the process against background noise, One of the most frequent mistakes is placing non-speech periods in the middle of a word or cutting the signal before the end of the word, in embodiments, this problem may be corrected by adding a hangover time. The basis behind this corresponds to the hysteresis rule, which keeps the label of the current frame as speech if the K previous ones were identified as such. It allows retrieving speech covered by noise and to improve the VAT) accuracy. The voice extraction task can be solved in a VAD equivalent approach.

In embodiments, the sound pressure level may be chosen as a feature vector and a decibel threshold as decision rule. Once the signal of the channel containing only the counsellor's voice goes beyond the pre-defined threshold, the mixed voices channel may be cut. The sound pressure level is expressed in dB and is computed by taking the logarithm in base 10 of the ratio between the sound pressure (signal amplitude) and a reference value ($p_{ref}=2\cdot 10^{-5}$, the lowest human hearable sound), the whole finally multiplied by 20, see Equation 10. No conceptual differences are induced by this scaling and it is meant to place the hearing threshold at 0 dB, $$L_p = 20 \cdot \log_{10}\left(\frac{p}{p_{ref}}\right) [dB] \quad (10)$$

Figure 5:
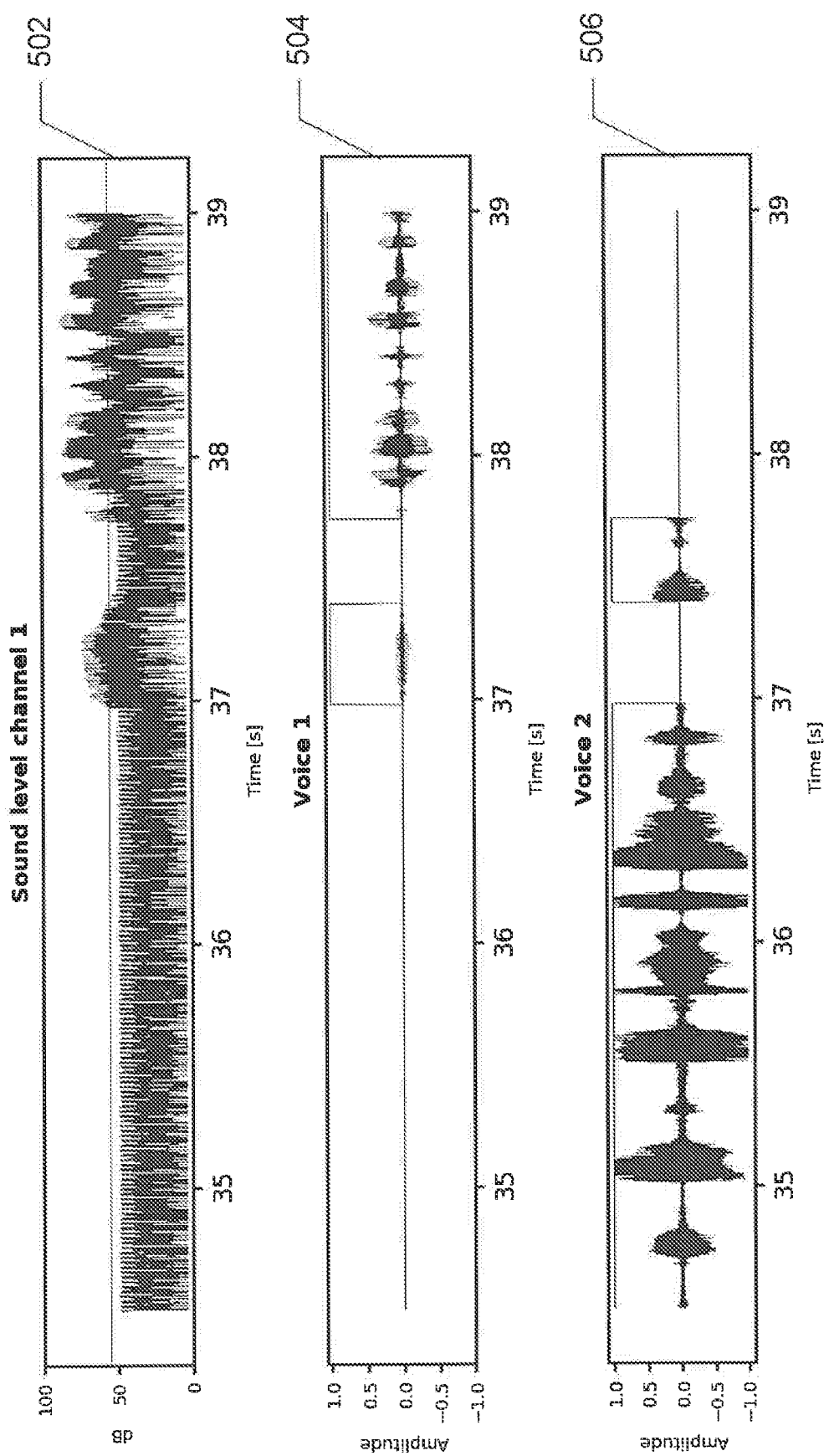
FIG. 5 is an exemplary illustration of VAD thresholding according to embodiments of the present systems and methods.

Determining the appropriate threshold has a significant impact on the algorithm performance. With a really high value, the detected samples are ensured to absolutely correlate with speech periods, but a large number of voice frames will be misinterpreted as silence. In terms of test statistics used to estimate the performance, this will lead to a large number of false negatives. On the other hand, a threshold set too low will guarantee identifying all speech periods. However, samples corresponding to background noise will probably be miss-labelled as speech, which would correspond to a high number of false positives in a statistics sense. The question is a matter of finding the right balance between false positives and false negatives. Human hearing is most sensitive in a frequency range between 500 and 4000 Hz and SPL going from 35 to 80 dB. The different sound pressure levels of human hearing are shown in Table 1. In embodiments, the value may be set to for example, 55 dB, which should catch the talking while removing the noisy parts, as shown in FIG. 5. For example, the sound level of a channel 1 is shown relative to the threshold value of 55 dB. Channel 1 includes voice signals of two voices, voice 1 and voice 2. Those features of voice 1 that exceed the threshold are captured 504 to form time periods in which voice 1 is speaking. The time periods other than when voice 1 is speaking may then be attributed 506 to voice 2.

TABLE 1

| Vocal | Decibels SPL |
| --- | --- |
| Hearing threshold | 0 dB |
| Whisper | 30 dB |
| Normal conversation | 50-70 dB |
| Shouting | dB |
| Pain threshold | 110-130 dB |
| Deafness threshold | 150 dB |

The main advantage of the thresholding method and the feature selected here is that it is fast and has a very low computational complexity, which are extremely important for real-time analysis. In embodiments, the voice extraction may be performed with the basic assumption of no co-occurring speech. If the counsellor is speaking, the probability that the caller is also speaking at the same time is presumed zero or very low. However, if the extraction results are poor, more elaborate features and a decision based on speech probability, such as performed in the OpenSMILE library, may be used in embodiments. In this case, if the probability of the channel containing only one voice is larger than a certain value, the signal on the other channel is shut down.

Pre-emphasis. One issue commonly encountered in speech analysis comes from the significant concentration of energy at the lowest frequencies of the voice spectrum. The speech signal has thus more energy and carries more important information in the low frequency range. Furthermore, the high frequency components are constituted of small amplitude relative to the low frequency elements. This difference of amplitude makes the signal processing and interpretation more difficult. In embodiments, this may be resolved by emphasizing the high-frequency information in embodiments, the method may be to simultaneously apply a high-pass pre-emphasis filter of first order as well as a gain to the audio signal. This results in boosting the high frequency energy by increasing the amplitude of the high frequency bands, while keeping the lower ones in their initial state. The pre-emphasis filter may be applied to the audio signal, for example, using Equation 11.

$$x_p(n)=x(n)-k \cdot x(n-1) \tag{11}$$

Figure 6:
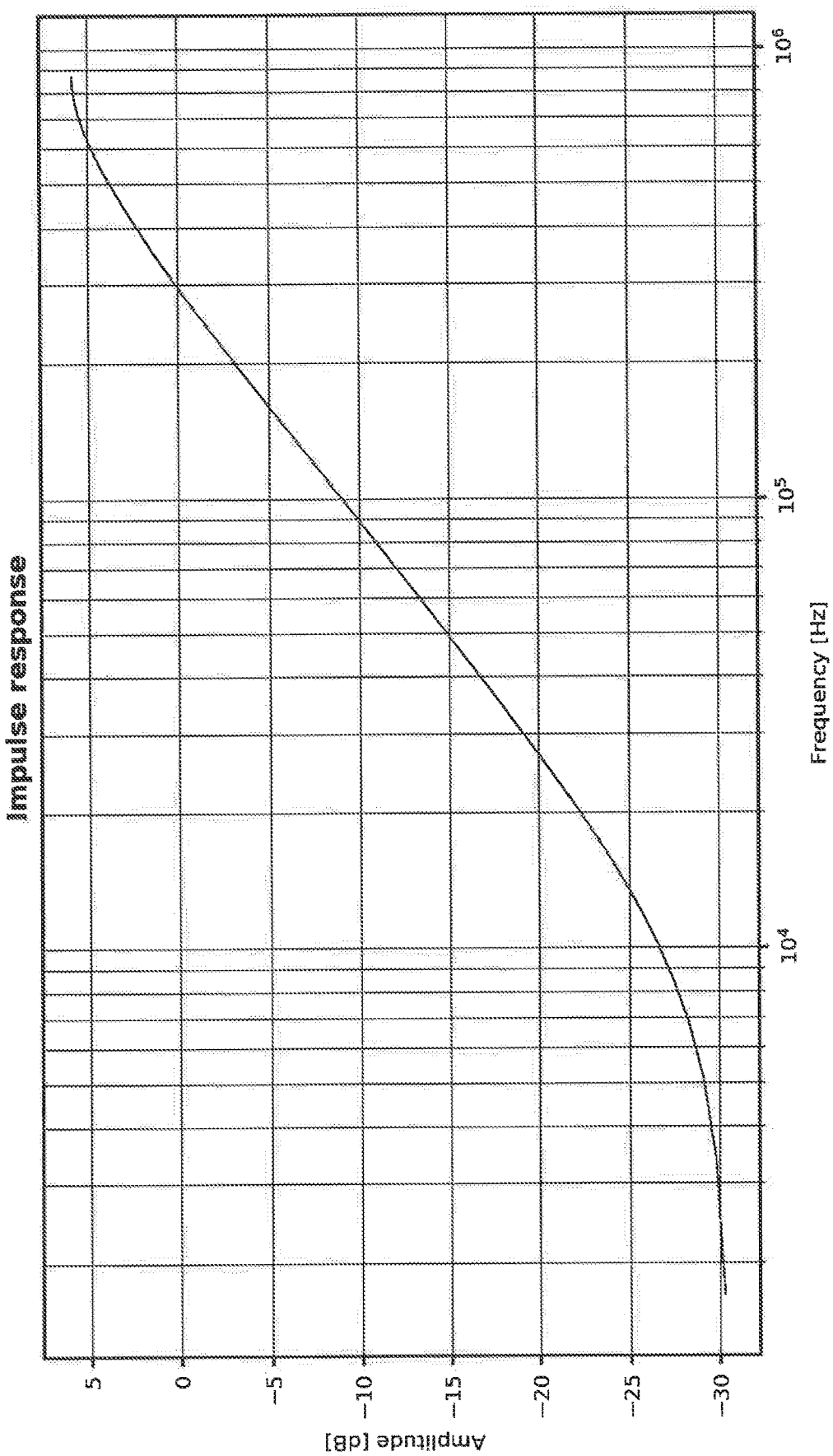
FIG. 6 is an exemplary illustration of the impulse response of a pre-emphasis filter according to embodiments of the present systems and methods.

The variable $k \in [0; 1]$ configures the pre-emphasis coefficient, which is usually set in a range from 0.9 to 0.97 for speech processing. This constant is referred to as the cutoff frequency of the filter and is intended to control its strength. The impulse response of this filter is based on Equations 12 and 13 is illustrated in FIG. 6.

$$h(n) = \delta(n) - k \cdot \delta(n-1) \tag{12}$$

$$H(f) = 1 - k \cdot e^{-j\frac{2\pi f}{f_s}} \tag{13}$$

The result is a more balanced spectrum. However, the main drawback of this approach is a potential increase of the noise in high frequency components, which alters the feature extraction and could affect the model accuracy. But in any case, noise is naturally more present at a lower frequency.

Figure 7:
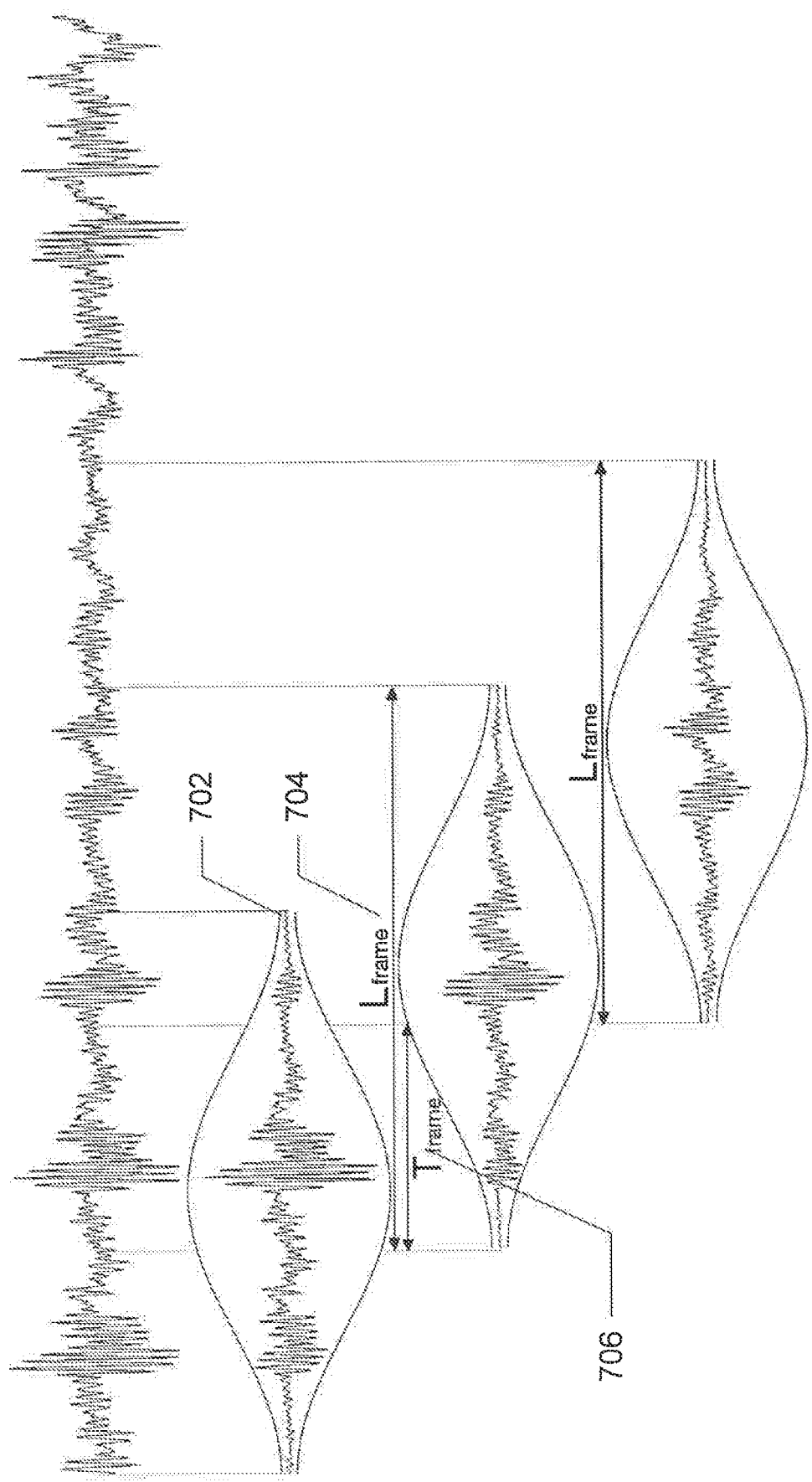
FIG. 7 is an exemplary illustration of framing and windowing according to embodiments of the present systems and methods.

Short-time analysis. Framing. Either in frequency or time domain, the speech signal constantly fluctuates over time and its properties are not constant or non-stationary. Therefore, analyzing the audio signal as a whole does not seem coherent and would induce information loss when considering the signal over a long period of time. However, on a short time scale, the signal and its characteristics vary only minimally, in embodiments, the speech signal may be partitioned into short-time frames to achieve local stationarity, Each frame may be considered individually and characterized by a distinct feature vector. As shown in FIG. 7, the signal x(n) may be cut into short overlapping frames 702, each containing $N_{frame}$ samples. $N_{frame}$ can be computed from Equation 14, where $L_{frame}$ 704 corresponds to the frame length measured in a unit of seconds.

$$N_{frame}=L_{frame} \cdot \text{Sampling rate} \tag{14}$$

The frame length may be defined sufficiently small to be able to be assumed to be stationary within a single frame, while not too short in order to provide a coherent spectral estimation. For the purpose of speech analysis application, frame lengths are commonly between 20 and 60 ms. In embodiments, it may be set to 25 ms, which is a common choice. As shown in FIG. 7, the time between two successive frames is represented by the frame period, $T_{frame}$ 706. The percentage of overlap between consecutive frames is derived from Equation 15. A typical frame period is of 10 ms, leading to an overlap of 60% in our case. The overall process is illustrated in FIG. 7.

$$\text{Overlap} = \frac{L_{frame} - T_{frame}}{L_{frame}} \tag{15}$$

The last point relates to the end of the sample. The question is how to handle the last group of samples being fewer than $N_{frame}$. The first and simplest approach would be to not take them into consideration, assuming that those samples at the end of the signal will not affect the outputs. Instead of discarding them, the system could be developed to manage a shorter last frame. In embodiments, the strategy may consist of extending the signal of $N_{frame}-N_{excess}$ zero samples, which would allow obtaining frames of equivalent length without ignoring samples.

Windowing. When applying Fourier Transform (FFT and TFT) to determine the spectral content of a signal, assumptions regarding periodicity and infinite duration have to be made. The signal is supposed to repeat with a period corresponding to the recording length. In reality and by necessity, observed signals are restricted to finite intervals, violating the Fourier Transform assumptions. Nevertheless, an observation interval being an integer multiple of a signal period should not induce any artifacts, while a non-integer multiple observation time can introduce alterations in the frequency components. This results in discontinuity in the time domain, which is referred as to spectral leaking in frequency domain. Looking at the representation in frequency domain, the spectral leakage can be seen by the presence of side lobes surrounding the main lobe.

In order to prevent those artifacts, a weighting function may be applied to each truncated waveform before the computation of the Fourier Transform. Multiplying the signal by a fixed length window may reduce the amplitude of discontinuities at the boundary of each frame. This means that it decreases the spectral leakage problem related to finite intervals. This filter has the effect of slowly and smoothly attenuating the frame edges towards zero. Among a large number of windows possible, the perfect function would not deform the spectrum. However, a trade-off between the time and frequency domain resolution of the window needs to be established. A window of finite length with abrupt boundaries, such as a rectangular window, is the simplest in the time domain, but creates artifacts in the frequency domain. A function such as the Dirac function, with a thin central peak and maxima tending towards zero elsewhere may be better in the frequency domain. But this type of function has infinite duration once transferred to the time domain, which does not correlate to an ideal time domain window function. Regardless of the selected window, completely avoiding spectral deformation is not possible and the window will not be of infinite length.

The simplest window function is probably the Dirichlet window, more commonly known as the Rectangular window. It is unitary within the observation interval, while setting all samples outside this defined region to zero, see Equation 16, leading to abrupt sectioning of the signal.

$$w_{rec}(n) = \begin{cases} 1 & n \in [0; N-1] \\ 0 & \text{otherwise} \end{cases} \quad (16)$$

Converted to the spectral domain, this window is equivalent to a sine function, Equation 17.

$$W_{rec}(m) = \frac{\sin(m)}{m} = \text{sinc}(m) \quad (17)$$

As its computation does not involve any multiplication, it is quite efficient and achieves better stationary resolution. However due to the undesired presence of side peaks of high amplitude in the frequency domain, it is more appropriate for speech analysis and feature extraction related to the time domain such as signal Energy, Amplitude or Zero-Crossing Rate, and thus does not really seem relevant for the purpose of this project.

In embodiments, a suitable window for spectral domain analysis may be the Hanning window, also called the raised cosine window. It is described by Equation 18, with both edges of the window reaching zero. In contrast to the rectangular window, it has the property to be a continuous function and so does its first derivative. Looking at the frequency representation, the sidelobes decrease by about 18 dB per octave.

$$w_{hann}(n) = \begin{cases} \frac{1}{2}\left[1 - \cos\left(\frac{2\pi n}{N-1}\right)\right] & n \in [0; N-1] \\ 0 & \text{otherwise} \end{cases} \quad (18)$$

Figure 8:
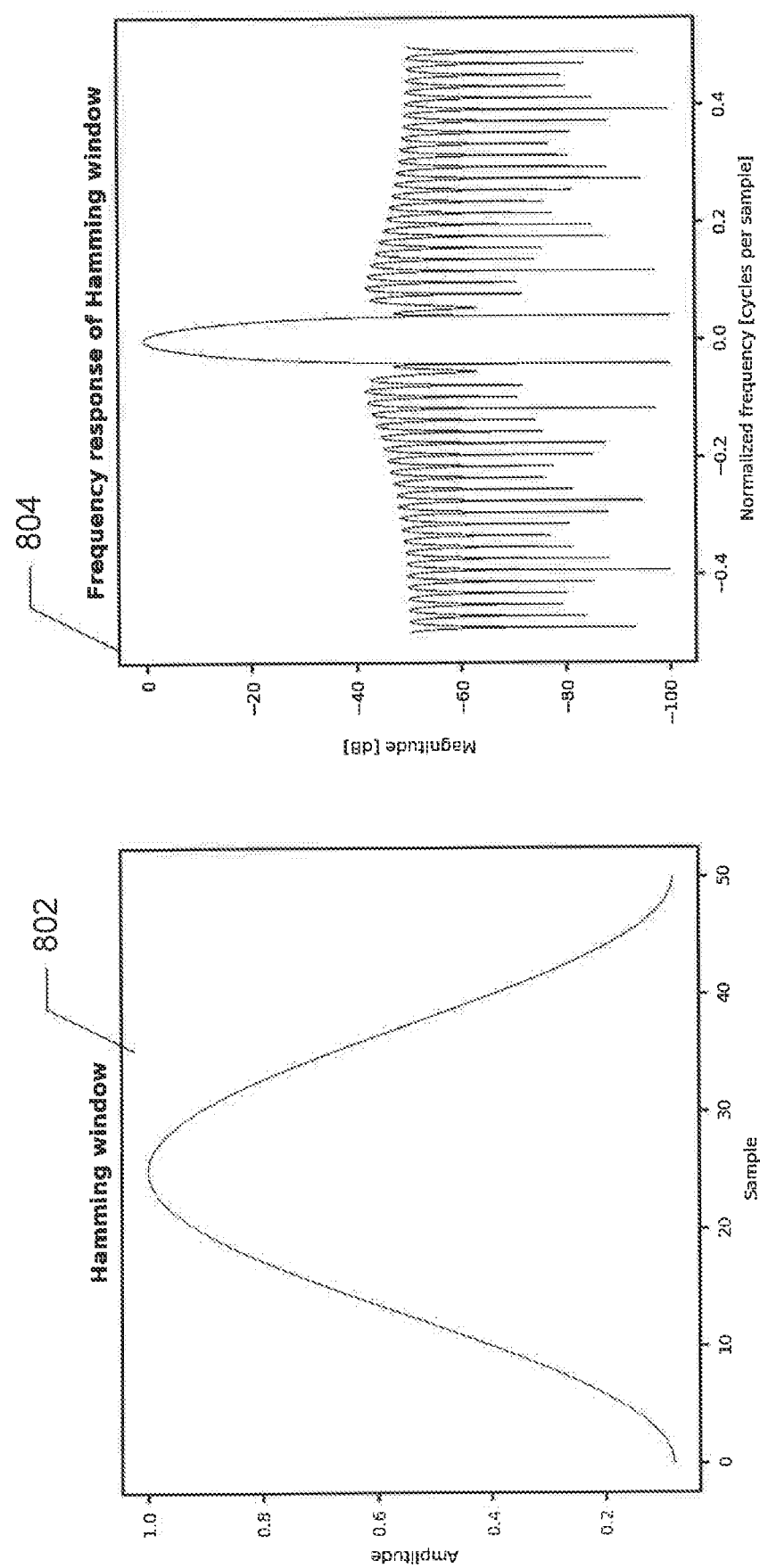
FIG. 8 is an exemplary illustration of a Hamming window and frequency response according to embodiments of the present systems and methods.

In embodiments, the Hamming window may be used, as it is the most widely used choice for spectral domain analysis and tasks more specifically related to speech analysis. It can be obtained by a simple modification of the Hanning Window, see Equation 19. The time domain form 802 of the Hamming window and the frequency domain response 804 of the Hamming window are shown in FIG. 8. Instead of using 0.5 for the variable $\alpha$ and $\beta$, those variables may be adjusted to minimize the first sidelobe amplitudes in the frequency domain. This is achieved at the cost of higher order sidelobes, but allows a better frequency resolution. The optimal coefficients are $$\alpha = \frac{25}{46},$$

which is usually approximated to 0.54, and $\beta = 1 - \alpha \approx 0.46$.

$$w_{hamming}(n) = \begin{cases} \alpha - \beta\cos\left(\frac{2\pi n}{N-1}\right) & n \in [0; N-1] \\ 0 & \text{otherwise} \end{cases} \quad (19)$$

The fact that its spectrum rolls off relatively fast makes it well suited for speech signal spectral analysis. Unlike the Hanning window and as shown in FIG. 8, the window edges do not attain zero amplitude.

Feature Extraction. Feature extraction is the process of applying digital signal processing methods to inputs in order to reduce the initial load, remove all redundancies and keep only the necessary information. This information is stored in, so called, acoustic features vectors reconstructed from the original audio signal. The purpose is to detect and capture any fluctuations of speech characteristics specific to mental or emotional states. A large variety of feature representations are available for this purpose. It is important to select the most appropriate and relevant set for the task in question, and the accuracy of the model varies depending on the feature combination.

There exist multiple possibilities for categorizing acoustic features. In an embodiment, the features may be divided according to the domain in which they are computed, either time (energy, zero crossing rate, etc.), frequency (fundamental frequency, Mel Frequency Cepstrum Coefficients (MFCC), PLP, etc.) or phase space. Another distinction can be derived from the auditive perceptual concepts in terms of speech quality (modality, tension, hoarseness, sharpness, etc.), prosody (pace, pitch, rate, pause frequency, etc.) or articulation (presence of reduction and elision, slurred speech).

Most of acoustic features are said to be Low-Level Descriptors (LLD), corresponding to speech features based on frame level (computed for short-time windows). Among common parameters suitable for extracting information from speech, Mel Frequency Cepstrum Coefficients (MFCC) and pitch (frequency of vocal cords vibration) are probably the most frequently used. Others are energy, fundamental frequency, formants, harmonic-to-noise ratio, etc.

MFCC. Mel Frequency Cepstrum Coefficients (MFCC) are highly studied and used in the field of speech, speaker and emotional state recognition or similar audio processing. This is probably due to its capability to be less sensitive to noise coupled with the high recognition accuracy it can achieve. This method is known for its ability to detect paralinguistic content in speech signal processing.

Besides its high recognition performance, MFCC has the valuable property to generally have uncorrelated variance between its coefficients. This means that unlike spectrum, there is no need to calculate the covariance between each feature, which leads to a great reduction in the number of parameters to compute.

The above characteristics are also known for their capability to isolate the filter from the source. Speech signals are generated by the passage of glottal waveforms of specific frequency through the vocal tract. Due to its particular shape, the vocal tracts act as a filter. A lot of information carried in the glottal source is not essential or relevant for recognition tasks, such as phones detection. Capturing the characteristics of the vocal tract filter would be the most useful information. It reveals the precise position of the vocal tract from which the created phone can be reconstructed. Effective feature representations would be able to separate the vocal tract filter from the source, which is the case of the cepstrum features.

Figure 9:
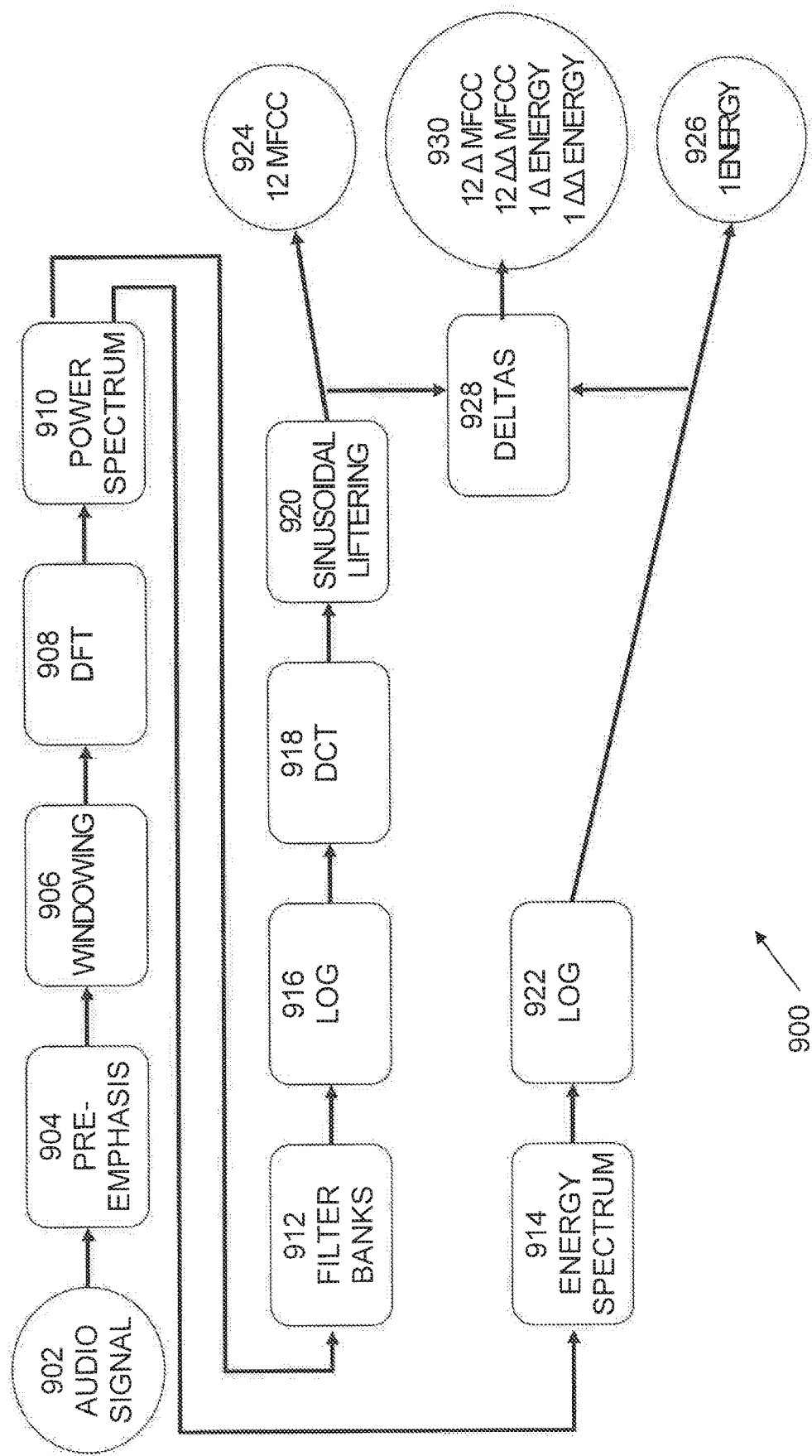
FIG. 9 is an exemplary block diagram of MFCC computation according to embodiments of the present systems and methods.

An exemplary block diagram of MFCC computation 900 is shown in FIG. 9. As shown in this example, an audio signal 902 is input to pre-emphasis stage 904, the output of which is input to windowing stage 906, the output of which is input to discrete Fourier transform (DFT) stage 908, the output of which is input to power spectrum stage 910. The output from power spectrum stage 910 is input to both filter bank stage 912 and energy spectrum stage 914. The output from filter bank stage 912 is input to log stage 916, the output of which is input to discrete cosine transform (DCT) stage 918, the output of which is input to sinusoidal liftering stage 920, the output of which is 12 MFCC data samples 924. The output from energy spectrum stage 914 is output to log stage 922, the output of which is 1 energy spectrum data sample 926. The outputs from sinusoidal littering stage 920 and log stage 922 are input to deltas stage 928, which generates as output 12 Δ MFCC data samples 12 ΔΔ MFCC data samples, 1 Δ energy spectrum data samples, and 1 ΔΔ energy spectrum data samples 930.

The algorithm is trying to mimic and be as close as possible to the process of frequency perception by the human auditory system. This representation of the speech signal is the linear cosine transform of a short-term log-power spectrum on a non-linear Mel frequency scale. After the pre-emphasis 904 and windowing 906 of the audio signal 902, the major steps required to obtain those characteristics are the computation of the power spectrum 910 and filter banks 912, followed by the discrete cosine transform 918 and finally a sinusoidal liftering 920, as shown in FIG. 9. These steps are described in more detail below.

Fourier transform and Power spectrum. MFCC, like many acoustic features, are computed from the spectral domain. The spectrum of the signal quantifies the amount of energy in each frequency band. However, the raw spectrum itself carries a lot of redundancy (strong correlation between features) and is not an optimal LLD descriptor. It is thus more favorable and relevant to use characteristics derived from the spectrum as feature vectors. The transformation from time to frequency domain is performed through the Fourier Transform. The outcome is a complex value that corresponds to the magnitude and phase of the signal. As the input in consideration here is a digital signal, the computation is achieved by the Discrete Fourier Transform (DFT), which is defined in Equation 20. N corresponds to the number of points used for the calculations and indicates the FFT size. It is typically set to 512.

$$X(m) = \sum_{n=0}^{N-1} x(n) e^{-\frac{j2\pi mn}{N}} \quad m \in [0; N-1] \tag{20}$$

Unfortunately, extracting spectral information via the DFT requires computations with asymptotical complexity, $O(N^2)$. Optimised algorithms were thus implemented. The efficient N-point Fast Fourier Transform (FFT) is based on the divide and conquer approach. By dividing the N-point DFT into two sub-computational pets, the complexity is reduced to $O(N \cdot \log(N))$. For audio signal processing, only the amplitude of the spectrum carried relevant information. Assessing the amplitude can be achieved by taking the magnitude of the DFT, as shown in Equation 21. The phase is non beneficial unless the application requires computation such as a precise reconstruction of the ordinary signal x(n).

$$X_{mag}(m) = |X(m)| \sqrt{1 m(x(m)^2 + Re(X(m)^2)} \tag{2}$$

The drawback of the spectrum is its linearity in the frequency and magnitude components. It is not a suitable representation of human auditory perception, which is highly non-linear. The idea is to obtain features that get as close as possible to the process happening in the human system. A better approach is to use the power spectrum, see Equation 22 for the computation. It represents the quadratic energy in each bin. The LLD is also normalized, to acquire a descriptor which is independent of the frame length.

$$X_p(m) = \frac{|x(m)^2|}{N} \quad 0; N-1 \tag{22}$$

Mel filtering. Human auditory perception is far from being linear, meaning that it is not equally responsive to all frequency components. Human hearing is more sensitive to lower frequencies, especially below 1000 Hz. Mel-filtering is like the human ear. It behaves as a series of band-pass filters, intensifying certain frequency bands. Those filters are irregularly distributed over the frequency range, with a greater concentration on the low rather than the high frequency side. Multiple algorithms have been implemented to represent the most realistic and relevant way in which human auditory system works. It has been proved that modelling this characteristic induces a net enhancement of audio analysis system performance.

One possibility to numerically describe non-linear human hearing perception is through the Mel-frequency scale. The mapping of Mel-frequency scale is defined almost linearly up to 1000 Hz, and above this value it changes into a logarithmic approximation. There is no single Mel-scale formula and various analytical approximations of this scale have been proposed. Whereas a non-significant difference in terms of performance was shown depending on the formula chosen, the transformation below, see Equation 23, demonstrated a more precise approximation for the frequencies lower than 1000 Hz, however less precision above this threshold.

$$f^{(mel)} = 2595 \cdot \log_{10}\left(1 + \frac{f}{700}\right) \tag{23}$$

$$= 1127 \cdot \ln\left(1 + \frac{f}{700}\right)$$

Figure 10:
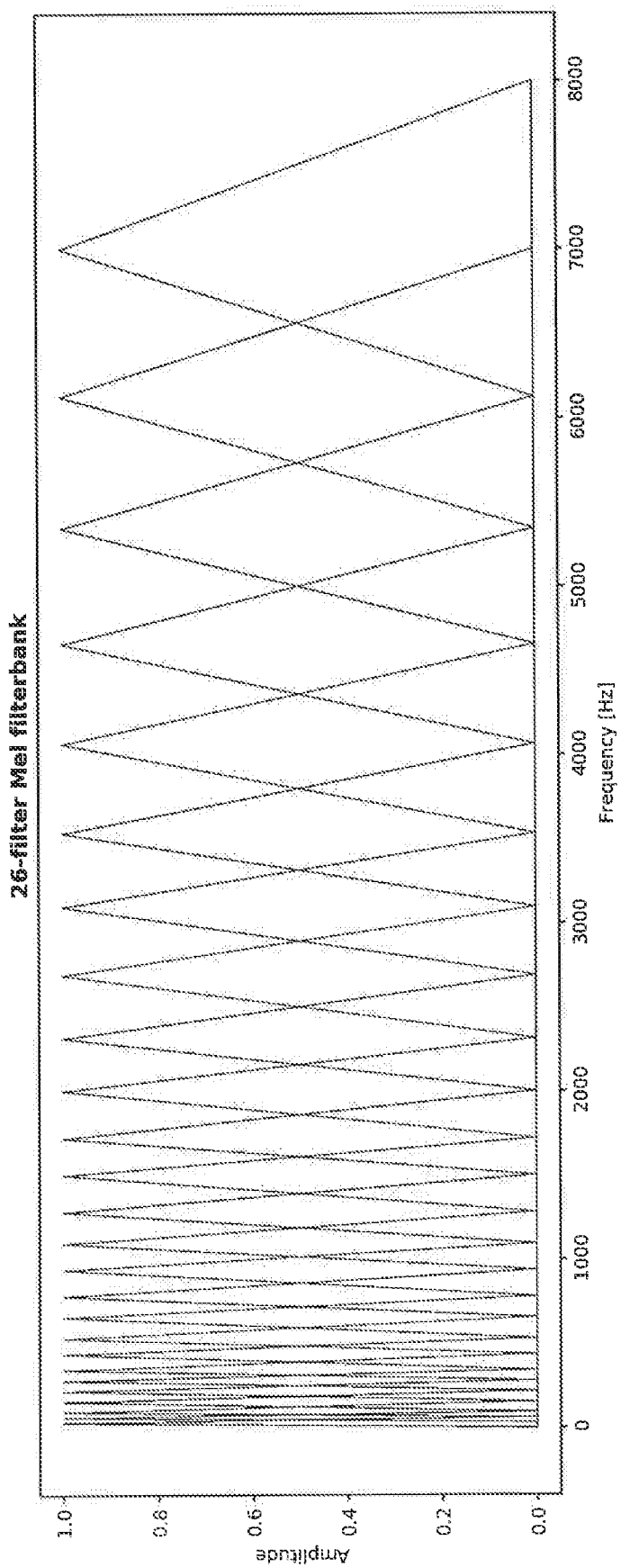
FIG. 10 is an exemplary illustration of a mel filterbank according to embodiments of the present systems and methods.

Mel-filtering aims to restrain the number of M frequency bands to a smaller number of B bins. Once the M bins power spectrum is defined, the approach is to convolve it with a series of B band filters, see Equation 24. The result provides an indication of the amount of energy present in each band. To get closer to the non-linear human frequency perception, the filter bandwidth generally enlarges as the central frequency increases, see FIG. 10 for a better visualization. This is implemented with a bank of filters, linearly spaced below 1000 Hz and logarithmically above this value. The filters are uniformly distributed in the Mel-frequency domain, while being non-equally spaced in the frequency domain. For the MFCC computation, it is typically a set of 20 to 40 triangular filters that is applied to the power spectrum. The gold-standard is 26. The filter bank is computed from Equation 25. By assuming a FFT length of 516, the filter bank consists of 26 vectors having a size of 257. Each vector will essentially contain zero values, except for a small portion of the spectrum, with a maximum amplitude of one at the center frequency and decreasing values that reach zero at the center frequency of the two neighboring filters.

$$X_p^{(mel)}(b) = \sum_{m=1}^{M} X_p(m) H_b(m) \tag{24}$$

$$H_b(m) = \begin{cases} 0 & m < f(b-1) \\ \frac{m - f(b-1)}{f(b) - f(b-1)} & f(b-1) \le m \le f(b) \\ \frac{f(b+1) - m}{f(b+1) - f(b)} & f(b) \le m \le f(b+1) \\ 0 & m > f(b+1) \end{cases} \tag{25}$$

The last step in obtaining the Mel spectrum is to apply the logarithm to each feature, see Equation 26. Human hearing is much more sensitive to small fluctuations in amplitude at low frequencies than it is at high frequencies. The logarithm is used to model this phenomenon. Furthermore, it helps to reduce the input sensitivity to variations. In order to avoid the problem caused by calculating the logarithm of zero and to prevent the presence of large negative number once the logarithm is applied, very small feature components are floored to the value $X_{floor}$. By default, this quantity is set here to the machine epsilon (eps). It corresponds to the lowest representable positive floating point so that $1.0 + eps \ne 1.0$ is satisfied.

$$X_p^{(log,mel)}(b) = \begin{cases} \log(X_p^{(mel)}(b)) & X_p^{(mel)}(b) < X_{floor} \\ X_{floor} & \text{otherwise} \end{cases} \tag{26}$$

Many multiplication and addition operations are necessary to calculate the Mel-filterbank spectrum. This step in the computation of MFCC takes about 90% of the total process, in terms of computational load and resource requirements.

The Mel spectrum could also be a possible feature representation for speech analysis. However, it has the undesired property of mostly having highly correlated coefficients, which is not the case of MFFC feature representations.

Discrete cosine transform. The next step would be to apply the Inverse Discrete Fourier Transform (IFFT) in order to transform the Mel-spectrum from the frequency domain to the spatial domain. However, the coefficients do not represent the full spectrum anymore. The current coefficients are log-energy information passed through Mel filter banks and do not contain any details regarding the phase. Applying the IFFT on those representations would result in complex values, which would not really be helpful for subsequent processing nor the obtention of compact indicators. For this reason, the Discrete Cosine Transform (DCT) is preferred, see Equation 28. Besides its advantage of returning real numbers, the DCT also has great properties of dimensionality reduction. The major part of the energy is condensed within the first coefficients, leading to compressed representations.

$$C^{(mel)}(k) = \sqrt{\frac{2}{B}} \cdot \sum_{b=0}^{B-1} X_p^{(log,mel)}(b) \cos\left(\frac{\pi k}{B}\left(b + \frac{1}{2}\right)\right) \tag{27}$$

The lowest spectral values contain information regarding the vocal tract filter that is well isolated from the glottal source, which is desired for phone detection problems. The higher Cepstral coefficients would be considered if the interest was pitch detection. In embodiments, only the first 12 to 16 Mel-cepstral coefficients are typically chosen, for example, with a value set to 12.

Sinusoidal liftering. The last step is applying a sinusoidal Hering to the cepstral representations. It is achieved using Equation 28. This filter has the effect of emphasizing the low order coefficients and therefore enlarging the amplitude of higher components. The outcome of this operation is the widely used speech analysis feature, Mel Frequency Cepstral Coefficients (MFCC).

$$C^{(lift,mel)}(k) = C^{(mel)}(k)\left[1 + \frac{L}{2}\sin\left(\frac{\pi k}{L}\right)\right] \tag{28}$$

Delta and Acceleration. The acoustic LLD computed so far are only representative of isolated frames. It is only the power spectral envelope of individual frames that is defined by the cepstral features. No contextual information regarding the preceding and following frames are considered in those feature vectors. Nevertheless, speech is not a signal which is constant over frames and its dynamics also carry important information. Indicators of the MFCC coefficients trajectories over time, such as slope or stop burst, can be effective cues. So by performing post-processing on the LLDs and appending them to the original features, the model accuracy may be improved.

The simplest derived descriptor capturing feature dynamics is the straightforward calculation of the difference between each frame, as in Equation 29.

$$d_1(n) = x(n) - x(n-1) \tag{29}$$

However, the most common approach is to extend the frame context for a more refined estimation. The difference is assessed and smoothed over a wider window of size W. Those derived LLD are called Delta Regression Coefficients and may be computed using Equation 30. The extent of considered context is defined by the window length, which also determines the smoothing impact. A small window will only reflect the short-range changes, while a broader size will catch the mid- to long-range dynamics of the LLD. For example, in the OpenSMILE toolkit, the window length is set to W=2.

$$\delta_1^W(n) = \frac{\sum_{i=1}^{W} i[x(n+i) - x(n-i)]}{2\sum_{i=1}^{W} i^2} \qquad (30)$$

The higher order dynamics also capture relevant information about speech. The derived descriptors may be enlarged to higher order differences through Equation 31, which computes the $j^{th}$ order delta regression coefficient with a window size W. For instance, the widely known acceleration coefficients are obtained by the second order derivative.

$$\delta_j^W(n) = \frac{\sum_{i=1}^{W} i[\delta_{j-1}^W(n+i) - \delta_{j-1}^W(n-i)]}{2\sum_{i=1}^{W} i^2} \qquad (31)$$

The remaining question is how to manage the derivatives of the first and last frames. The solution relates to the method of padding. The idea is to repeat the border values or extend the feature vector with zeros in order to always be able to compute the difference. The number of repetitions depends on the window size W.

Spectral Energy. In addition to the MFCC coefficients, spectral energy and its deltas can also be computed as features vectors. Spectral energy represents the acoustic energy distribution across the frequency range. This type of characteristic is strongly correlated to phone identification. Vowels and syllables are known to contain a high level of energy relative to an unvoiced signal. Accordingly, the energy spectrum of speech parts should be larger than speechless parts. This can greatly help with detecting voice from silent parts in speech and improving the model performance.

As illustrated in FIG. 9, multiple steps are equivalent for computing the MFCC and Spectral Energy features. Based on the approach developed in the YAAFE toolkit, the computation is decomposed into steps. And the Spectral Energy can be directly calculated from the Power spectrum, see Equation 32, instead of the original audio signal. The big advantage of such implementation is the reduction in the computation complexity and storage requirements by avoiding redundancies.

$$E_{spec} = \sum_{m=0}^{N-1} X_p(m) \qquad (32)$$

Similarly to the Mel-filtering representations, the logarithm is applied to the spectral energy coefficients in order to get closer to the human hearing system, Equation 33. Once again, to avoid generating large negative numbers when executing this operation, the energy values are floored to $E_{floor}$, which is commonly set to the machine epsilon value.

$$E_{spec}^{(log)} = \begin{cases} \log(E_{spec}) & E_{spec} < E_{floor} \\ E_{floor} & \text{otherwise} \end{cases} \qquad (33)$$

Real-time analysis. The implementation of embodiments of the present systems and methods (signal pre-processing, feature extraction, etc.) may provide the capability to achieve an on-line system, which means continuous processing is occurring simultaneously while the data is being recorded. Opposite to off-line processing, multiple pass or contextual algorithms may not be used in on-line processing. Embodiments may give real-time feedback during the hotline call in order to help the counselor to judge the crisis level and to make decisions. Embodiments may return a severity index indicating the caller's suicidal impulse, as well as feedback related to the counsellor's apprehension, as close as possible to real-time.

Real-time processing corresponds to the processing of data at the same time as an event is occurring. This requires very fast processing with a lag time that is as small as possible. A typical delay is in the range of 100 ms to 10 s for speech analysis. For example, a way to assess on-line performance is through incremental algorithms. The idea is to reduce as much as possible the delay between data recording and system output, by processing the data as soon as it is available.

Multiple constraints appear with real-time and incremental processing conditions. The first one is the identification of speech segments and speech pauses during continuous audio streaming. Limitations may also come from the feature extraction process. In embodiments, all feature representations may be extracted in a single pass process, farther complicating the process. Specified modification of regular signal processing methods may be implemented. For example, the mean values for normalization can be roughly estimated first, while being constantly updated as new data are added. More modifications may be necessary to reduce the processing lag to an acceptable value for certain feature computation. However, the two feature types computed in embodiments of the present systems and methods, which are MFCC and spectral energy, are not affected by this issue. However, for the computation of delta and acceleration derivatives, the context has to be restricted to only a small number of frames. Features post-processing is subject to similar issues.

The realization of an on-line system depends mainly on the rapidity and computational complexity of its algorithm. Each step of the data processing has to be fast enough to avoid a constant increase of the delay between the incoming data and the output value, decreasing the usefulness of the system. The efficiency of the process is principally based on the framework architecture. Typically, data are accumulated in a buffer and outcomes are produced each time the buffer is filled. In addition to the feature extraction and classification complexity, the buffer size also contributes to the determination of the system lag.

Figure 11:
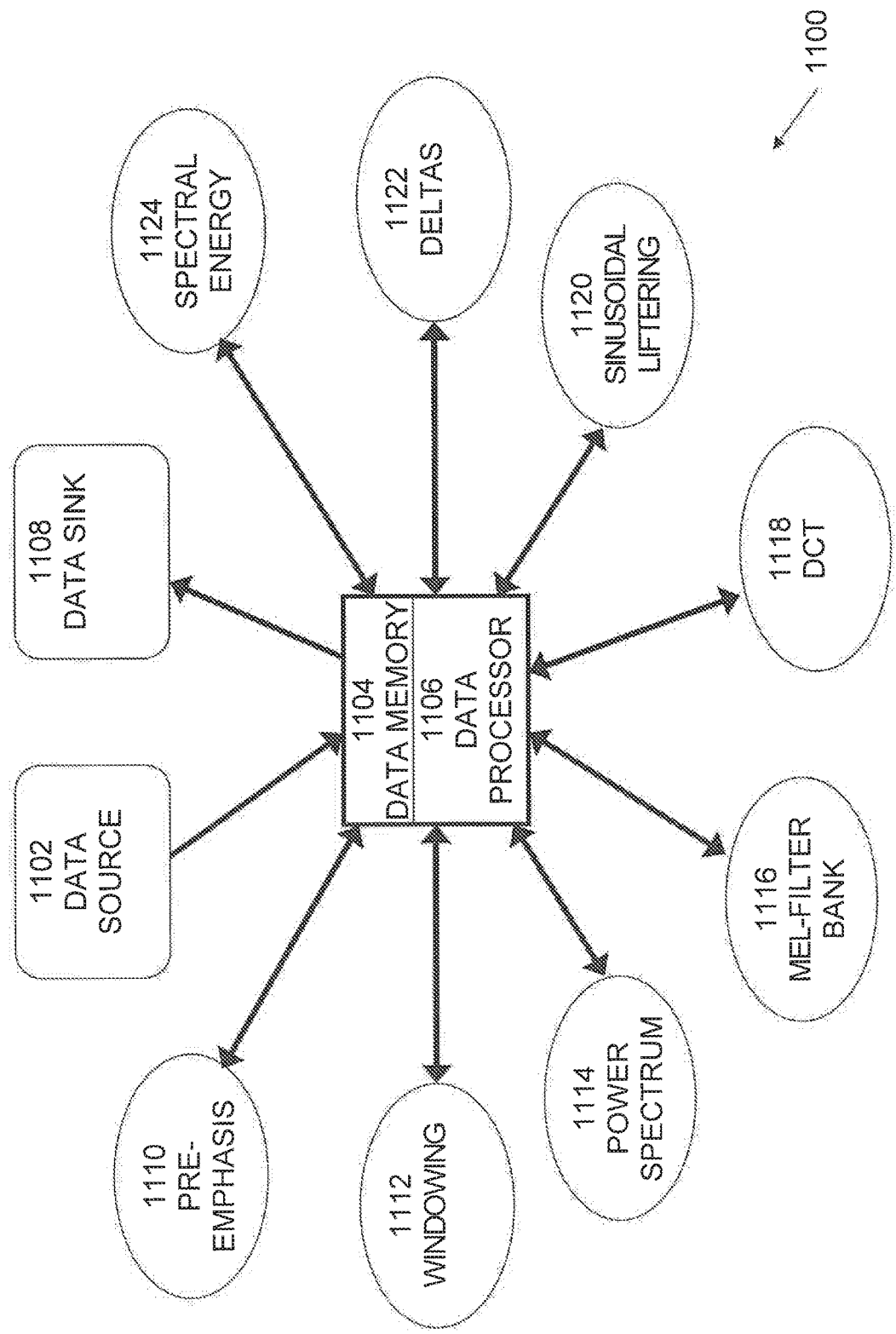
FIG. 11 is an block diagram of a system architecture according to embodiments of the present systems and methods.

An exemplary block diagram of a system architecture 1100 in which embodiments of the present systems and methods may be implemented is shown in FIG. 11. The basic idea of an incremental architecture, such as in, for example, the OpenSMILE library, relies on major components such as data source 1102, data memory 1104, data processor 1106, and data sink 1108. The incoming data may be generated by data source 1102, which writes them into data memory 1104. From data memory 1104, the data frames are processed and modified by data processor 1106 and backed up. Finally, the results are computed by data sink 1108, which either transfers the data from memory to an external operator or performs the classification itself. The interest of using data memory as a central component is to improve the computational and storage efficiency, leading to a robust data-flow.

The same data may be used multiple times, eliminating computational redundancies. It is a similar approach as the one implemented in the YAAFE library. For example, the Fast Fourier Transform (FFT) does not need to be performed twice for the MFCCs and spectral energy extraction. Embodiments of the present systems an method may include processing such as pre-emphasis 1110, windowing 1112, power spectrum computation 1114, mel-filter bank 1116, discrete cosine transform (DCT) 1118, sinusoidal littering 1120, deltas computation 1122, and spectral energy computation 1124.

In embodiments, this kind of architecture may be provided through the powerful mechanism of Threading and Queues of TensorFlow. A queue is like other elements in TensorFlow, a node in the TensorFlow graph that can be modified by other nodes. But the particularity of this node is its capacity to easily add new or remove existing items from the queue. The queue can be seen as the buffer or the data memory for storing elements and allowing efficient dataflow.

A TensorFlow session may be said to be multithreaded. This means that one session can be the executive element of multiple threads, which allows operations to run in parallel. As the data preparation is known to be time consuming, the typical mechanism consists of pre-processing the data by multiple threads, which then push it into the queue. At the same time, ready-to-use data can be pulled out from the queue for training. In reality, critical issues arise from the multithread session, such as catching exceptions or stopping a thread properly. Those are handled by QueueRunner and Coordinator elements. The QueueRunner, more particularly, consolidates the enqueuing process by multiple threads, while the Coordinator helps the ending process.

An example of a basic computational process is as follows. First comes the definition of the queue, with enqueue and dequeue operation nodes, then the QueueRunner is built. Finally, the TensorFlow session and the coordinator are generated. The QueueRunner can initiate multiple enqueue node threads and the dequeue operation can be executed, until the coordinator terminates it.

Figure 12:
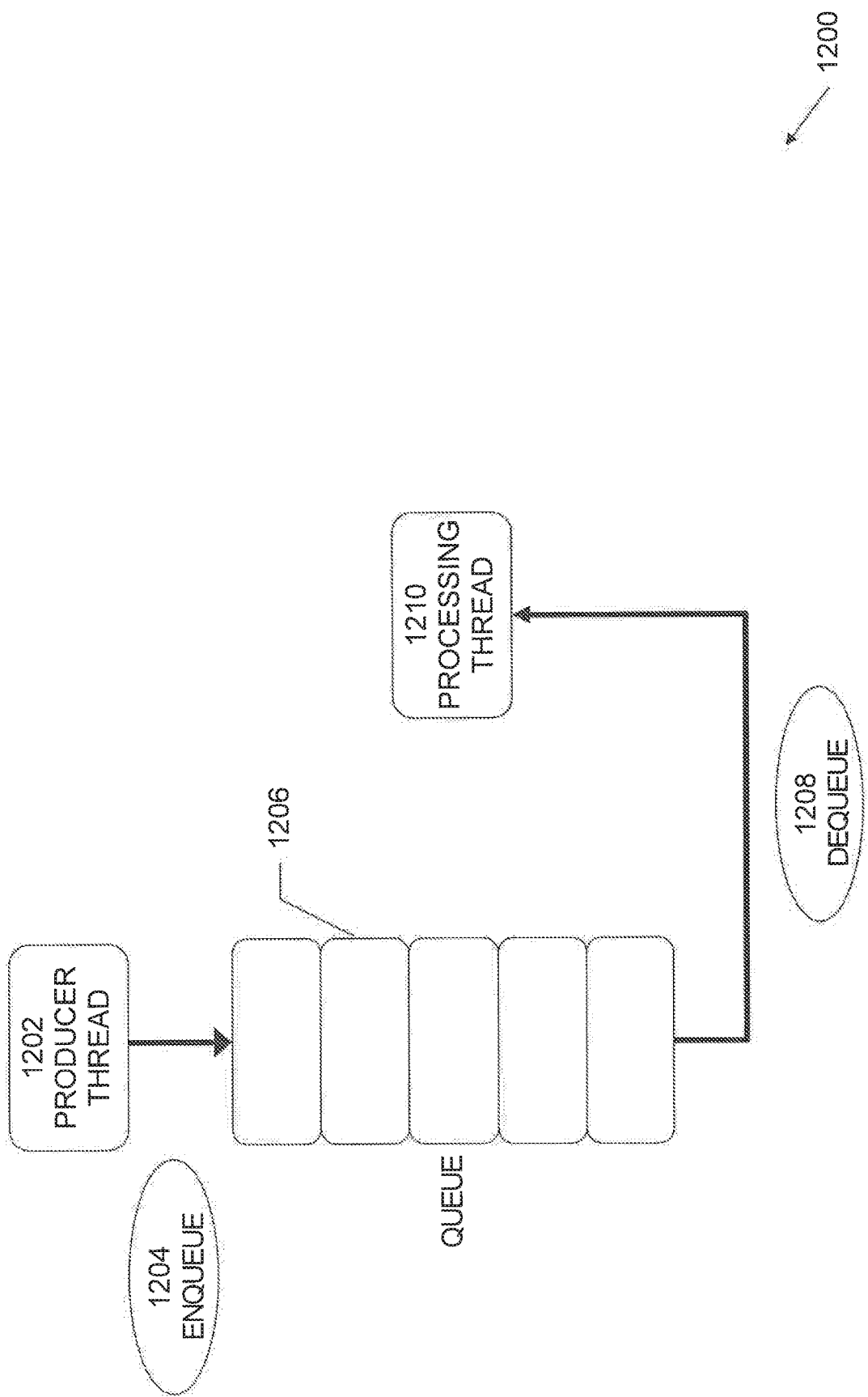
FIG. 12 is an exemplary block diagram of a Threading and Queue system according to embodiments of the present systems and methods.

One of the principal challenges in on-line processing is to manage continuous data flow. All of the data are not available at once, and the system should simultaneously control the processing of data in the memory and the loading of new data. For example, the TensorFlow Threading and Queues architecture may provide such functionality. This is a mechanism of memory optimization that can speed up the training process by about 30%. With a pool of threads, not only a net improvement of the model performance can be achieved, but also the execution latency is greatly reduced. An example of such a queueing scheme 1200 is shown in FIG. 12. A producer thread 1202 is in charge of continuously updating the system as new short recording sequences become available. The inputs are enqueued 1204 and kept in memory within queue 1206 until being dequeued 1208 by a processing thread 1210 for further computation. With this type of implementation, elements are constantly added to or removed from the queue 1206, not necessary at equivalent rates. However, the overall memory load remains constant, principally due to the restricted storage capability of the queue. This is particularly important in on-line processing, as the memory load typically affects the computational time. Keeping all the recording sequence in memory can typically lead to an overload of the system and an increasing time delay between incoming data and output.

Evaluation. In order to prove the relevance of the developed feature set, it will be evaluated with a simple model and task. The most studied task in the field of speech analysis is probably Automatic Speech Recognition (ASR). It is not, however, the ultimate goal of embodiments of the present systems and methods, which is namely giving feedback regarding the crisis situation in suicide hotline conversations. Nevertheless, both approaches are trying to capture the important and necessary characteristics in speech to perform a specific task. ASR will help to estimate the applicability of this work more easily.

In embodiments, a simple bidirectional Long Short-Term Memory Recurrent Neural Network (BLSTM-RNN) may be implemented to transcribe audio file from a well-known dataset into written sentences. The system may be built based on an example implemented by P. Rémy, with adaptations to include the set of features developed here and a BLSTM-RNN. The choice of the model is explained in more detail below.

Dataset Corpus. The idea of Automatic Speech Recognition is to build a system capable of transcribing speech into textual representation. The training of such a model requires a dataset that contains digital audio files, used as inputs, and their written transcriptions for the labels. For Neural Network modelling, the prediction performance may be enhanced with a larger number of samples. The more training samples, the better. Introducing more variabilities to the inputs (accents, intonations, spoken contents, etc.) will also result in a more generalized system. A certain number of datasets containing English speech recordings and their labels are freely available. Examples include LibriSpeech, CSTR VCTK and TED-LIUM.

In embodiments, the CSTR VCTK Corpus may be used. This database was constituted by the Centre for Speech Technology Research (CSTR) for the development of the Voice cloning Toolkit (VCTK), and is accessible under the Open Data Commons Attribution License. It contains the recordings of sentences read out loud by native English speakers. To ensure variability, a total of 109 speakers with diverse accents were involved. Each contributor read 400 newspaper sentences, the Rainbow Passage, and specific sections to identify their accent. The set of newspaper sentences is different for each speaker and was randomly selected from *The Herald* by an algorithm guaranteeing contextual and phonetic diversity. The same recording setup and parameters were used for everyone's recording, which took place in the same room at the University of Edinburgh. This database was developed with the intention of Hidden Markov Model (HMM)-based text-to-speech synthesis systems, which may be applicable to embodiments of the present systems and methods.

Before feeding the Neural Network, the input speech data are converted into Mel-Frequency Cepstral Coefficients (MFCC). It is this matrix of feature vectors that is given as input to the model.

Neural Network. As the desire is to also consider the dynamics and context of the signal, dynamic modelling may be preferred over static modelling. Instead of using a unique vector to map a label, in dynamical modelling, a set of feature vectors is aligned with either a label or a sequence of labels. This concept represents the dependencies between labels with regard to the inputs. In research fields associated with Automatic Speech Recognition (ASR), the Hidden Markov Model (HMM) is probably the most considered method for dynamic modelling. However, with the growing interest and researches on deep learning, Neural Network became a good alternative to HMM for dynamical modelling. A great advantage of Neural Network. Is that, apart from the selection of inputs and outputs, no other knowledge of the data is required. In a basic feed-forward Neural Network, no information other than the running time-step is considered. A simple Neural Network is said to have no memory. The model was thus further developed to incorporate recurrence by adding feedback from the previous time-step to the current input. This type of network architecture is referred as Recurrent Neural Network (RNN). With the addition of temporal contextual information, RNN became a powerful tool for modelling sequential data, it is particularly important for time series data to have the capability to store the past information and use it to influence the prediction. Due to its temporal nature, this type of Neural Network seems to be a good approach for Automatic Speech Recognition tasks.

Nonetheless, training a conventional RNN with a gradient back-propagation algorithm can be challenging and as the model undergoes the Vanishing Gradient Problem. The main idea of back-propagation is to adjust the weight according to the gradient error. In practice, the Gradient becomes smaller and smaller when propagating to deeper layers of the Neural Network. If the value tends to get too small, the learning becomes so slow that it stops working. Due to the Vanishing Gradient Problem, the network has access to a restricted temporal context of about 10 frames.

Figure 13:
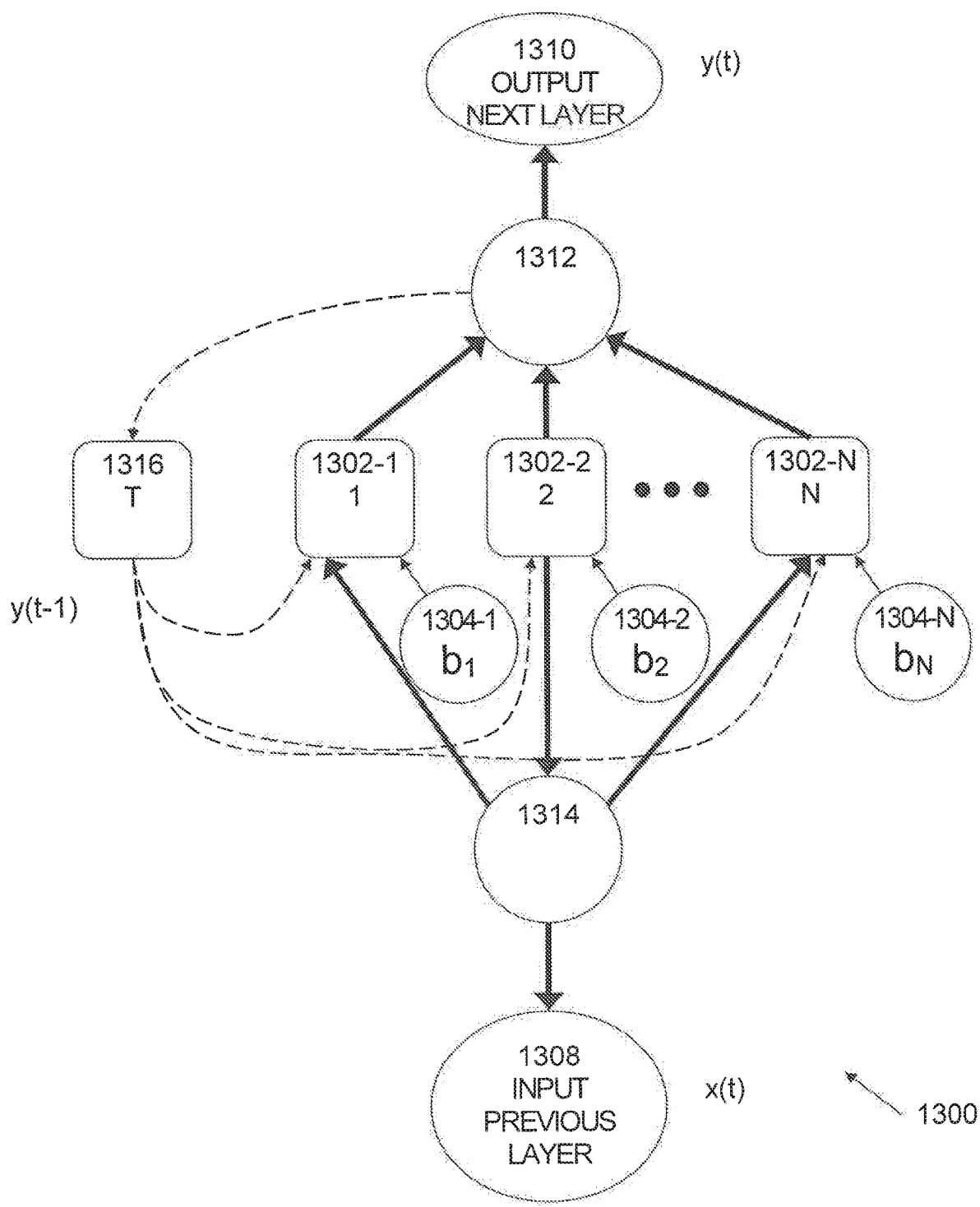
FIG. 13 is an exemplary block diagram of a central element of an LSTM block according to embodiments of the present systems and methods.

This problem was solved with the appearance of Long short-term memory (LSTM)-RNN. The elementary unit of LSTM-RNN is the LSTM block, an example of which is shown in FIG. 13. The central element of each LSTM block 1300 is the internal cell memory 1302-1-N, thanks to which the block should, in theory, be able to keep information for an infinite duration. In addition, the LSTM block contains multiplicative gates 1304-1-N to command the flow to the memory cell. The weighting of input 1308 and output 1310 is respectively controlled by input and output gates 1312, 1314. The forget gate 1316 manages the decay of the information stored in the memory cell, by forgetting or resetting the cell when necessary. A typical LST-RNN model contains N blocks, where each block is fully connected to the whole input set and recurrently linked to the outputs. With such a network, the long range connections of the input data can be exploited. This may be important in Automatic Speech recognition and translation tasks, where each time-point is highly dependent on its neighbors.

However, regular LSTM-RNN are only exploiting the previous context. Why not also consider the up-coming context? Particularly in Speech recognition and translation tasks, for which the utterance is decoded as a whole. Bidirectional Long Short-Term Memory Recurrent Neural Network (BLSTM-RNN) performs this function. The bidirectionally is achieved by incorporating two different hidden layers. The first one will process the sequence forwardly, while the second one backwardly. The past and future information can thus be assessed. Globally, with a bidirectional LSTM-RNN, long-range context in both directions can be reached, which is especially interesting when handling data with de-synchronization between input and output.

Connectionist Temporal Classification. Another problem arising with conventional RNN is the incapability to immediately assess the sequences. The inputs have to be pre-segmented before the training and the outputs post-processed to obtain the correct sequence prediction. This is principally due to the common network objective functions, which have to be defined independently for each sequence point. This constraint highly limits the use of RNN for diverse applications. To overcome this issue Connectionist Temporal Classification (CTC) may be used.

Instead of phonetic-based transcription, the incorporation of CTC allows performing character-level predictions. The objective function is utilized by the Neural Network to maximize the probability of finding the correct transcription. The network weights are then updated by computing the error rate from the predicted and true character sequences. The character-level error used here will lead similar results than the classic Levenshtein word error distance in languages, where each sound represents a specific character (phonetic language). But in the case of non-phonetic languages, such as English, those two measurements will differ. The model selects the most likely transcription based on a single time-step decision. The intuition of CTC is based on a softmax layer giving at distinct probability at each time-step of the sequence. Here comes the first difference compared to standard objective function, the model does not necessary have to make a character prediction, blank label are possible by attributing a probability of zero. Afterwards, with a Forward-Backward algorithm, all the potential probability sequences are summed and normalized, to result in the probability of the target alignment knowing the input. Instead of the log likelihood training optimization criterion, CTC is based on the log probability of state sequences. A BLSTM-RNN trained with a CTC objective function removes the requirements of pre-segmentation and post-processing. This type of model is well suited when the alignment between the audio inputs and target transcriptions is unknown.

Label Error Rate. In embodiments, an error that may be utilized is the Label Error Rate (LER). For a temporal classifier h and a particular sample set S', this measure is defined as the mean normalised edit distance between the model predictions h(x) and the target sequences y, see Equation 23. The edit distance ED (a, b) corresponds to the minimal number of insertions, substitutions and deletions necessary to transform a sentence a into a sentence b.

$$LER(h, S') = \frac{1}{|S'|} \Sigma_{(x,y) \in S'} \frac{ED(h(x), y)}{|y|} \qquad (34)$$

TensorFlow. The particular success of machine learning and deep learning in the recent years comes in parallel with several improvements. First, more and more data is available. The data flow comes from all around, from all kinds of devices and systems. Secondly, the computational capacity is continuously expanding. Some limits seem to have been reached for CPU speeds. Nevertheless, the systems are now exploiting the concept and parallel processing and the use of Graphics processing units (GPU). The theoretical and mathematical notions at the base of deep learning have been developed for some time. Neural Networks are powerful and give the model the possibility to utilize the data in the most valuable way. However, the capability to use such models more efficiently than other machine learning methods emerged more recently with the progress in computational power and the increased availability of data. This emerging capacity has led to the development of novel deep learning libraries. Even though all of them are devoted to build and train Neural Networks compromises between flexibility and productivity was always necessary. Either flexible but slow or efficient and non-adjustable.

TensorFlow was introduced as an open source library, somewhat solving this trade-off problem. The first public implementation was released in November 2015 by Google. And since them, it has turned into, what is probably, the most widely used deep learning programming library. Its use continues to grow in diverse fields. Whether in research or manufacturing, it turns out to be particularly interesting for "artificial intelligence, language processing, computer vision and predictive analytics". Improvements are constantly added to the library by many developers in order to achieve large efficiency and flexibility. Flexibility comes with the fact that the library is not only runnable on supercomputers, but also on embedded systems. Huge database can be powerfully utilized to train models. And it takes advantage of CPU and GPU processors. Important advantages of this library are also its great debugging and visualization capabilities. The basic concept of TensorFlow is not to furnish a black-box for solving machine learning problems. But to give the possibility to develop personalized model starting from basic mathematics. Other complicated computations than machine learning functionalities can also be accomplished.

In embodiments, TensorFlow may be used as the main python library for the feature extraction and model implementations.

Results. Pre-processing. Based on how the information is stored in a digital stereo wave file, as shown in FIG. 2, namely alternating between channel 1 and 2 samples, splitting the stereo audio recording into two mono signals is not a difficult process to achieve.

The challenging part comes with the voice extraction, which is necessary to be able to analyses the two speakers separately. As a reminder, the first channel contains the counsellor's voice, while the second one contains both voices, the counsellor's and the caller's. In embodiments, the extraction may be performed by phase inversion. This approach will be successful only if a perfect alignment in time and amplitude of the channels is obtained. Otherwise, it will not be possible to correctly or completely remove the counsellor's voice from the second channel.

The time correction may be performed by computing the absolute maximum of the cross-correlation between the two channels. In embodiments, the time shift may, for example, be estimated to be 39 samples, which corresponds to $8.84 \cdot 10^{-4}$ seconds. It is a very small value, which is not visually or audibly perceptible. However, it will still alter the phase inversion if this correction is not applied.

Figure 14:
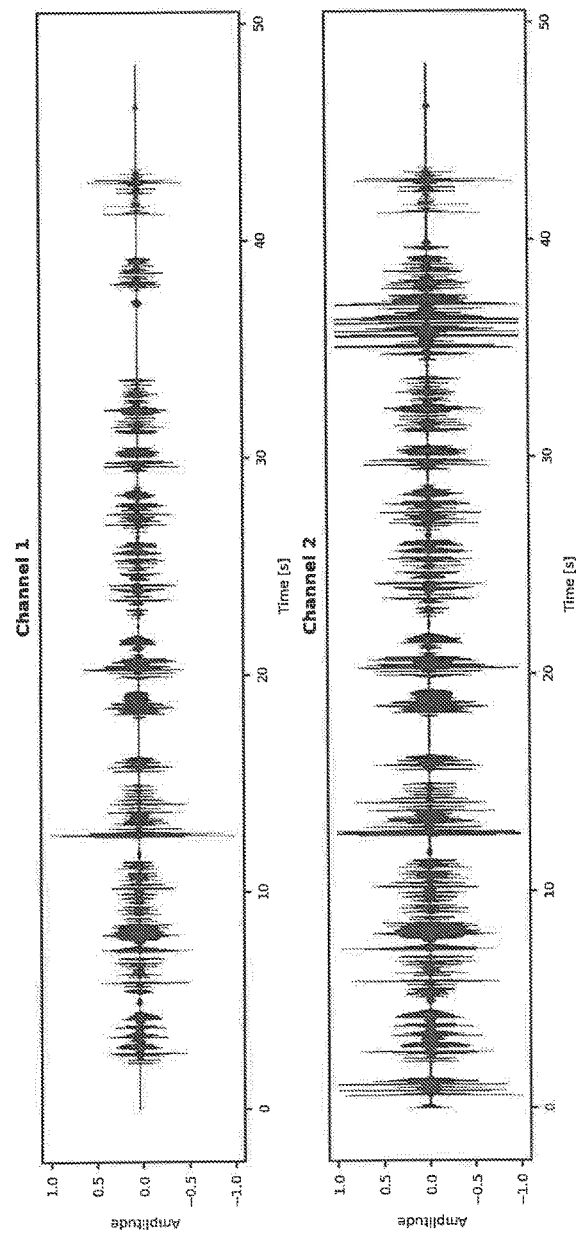
FIG. 14 is an exemplary illustration of channel gain difference according to embodiments of the present systems and methods.

As can be seen in FIG. 14, the gain difference is more discernible. The idea is to assume a linear relation between the two channels. The gain difference would then be the coefficient needed to cancel the channels, see Equation 3. The first naive method to determine this coefficient is to compute the difference of amplitude at any random instant t. This may be a non-accurate estimate. The value fluctuates considerably according to the diverse attempted instant t. In another approach, the coefficients obtained by minimizing the L-1 and L-2 norms, as above, are then compared. A segment containing only the counsellor's voice should be considered to obtain relevant results. The value computed with the L-2 norm is −2.54, while the one with L-1 norm is −2.51. In embodiments, the value obtained with L-1 norm minimization may be more precise and may be chosen as the multiplicative factor for the gain difference correction.

The time shift and gain difference coefficients should be unique to the recording device and should not change with different wave files. This implies that they only need to be computed once and they can then be used as a constant for the alignment of the two channels in the remaining part of the project. This greatly reduces the computational time and complexity of the global process.

Figure 15:
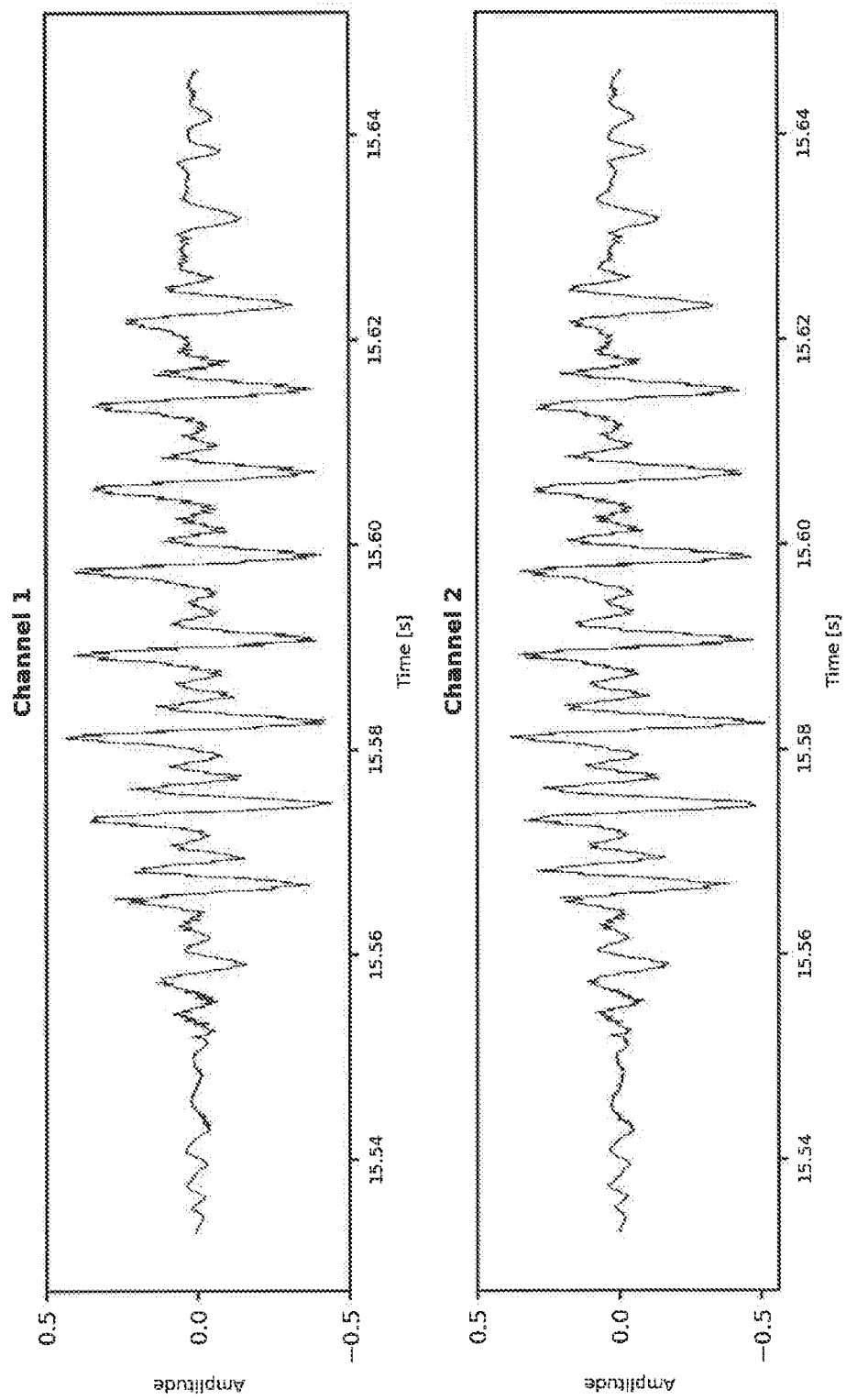
FIG. 15 is an exemplary illustration of dynamic difference between channels according to embodiments of the present systems and methods.

Once the channels are properly aligned, the phase inversion is tested to separate the two voices, see above. This approach allows isolating the counsellor's and caller's voice even from segments where the two are speaking simultaneously, which is highly favorable as no information is neglected. Furthermore, this does not required a lot of computation, which is important for the system efficiency and on-line processing. Unfortunately, the extraction of the two voices by phase inversion method is not successful here. The reason is mainly a difference of dynamisms and distortions between the two channels. To illustrate this, a short segment of both channels, containing only the counsellor's voice, is isolated and plotted in FIG. 15. Note that these two segments, although very similar, are not as identical as expected. The cause of this difference is not completely clear but it probably occurs during the recording process.

Figure 16:
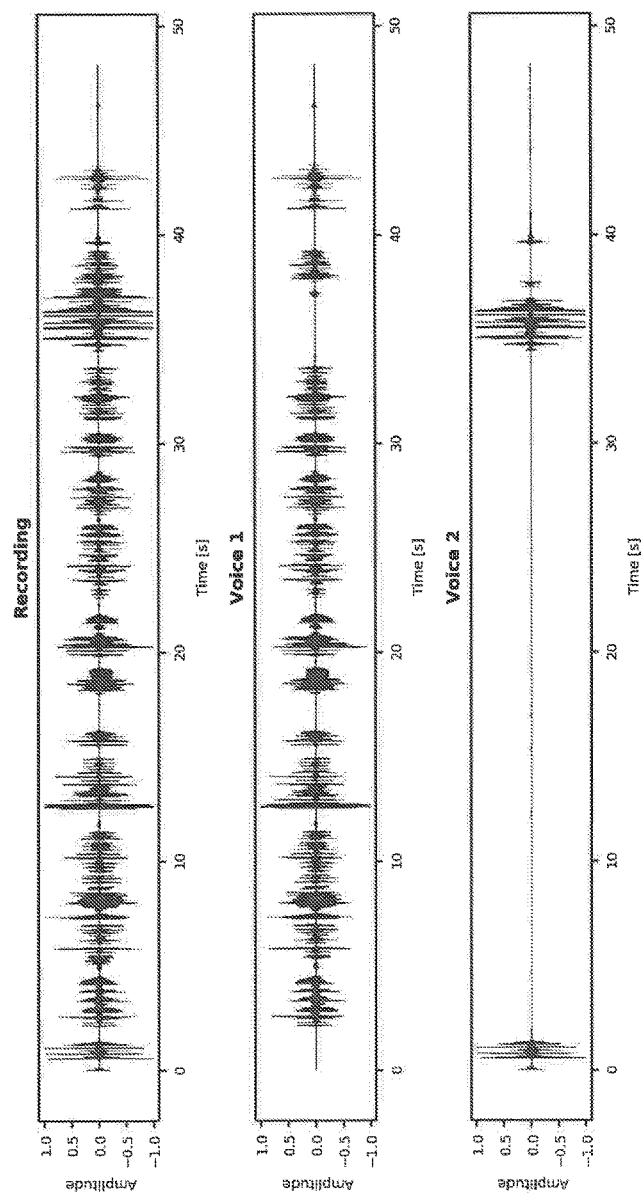
FIG. 16 is an exemplary illustration of voice extraction from a recording according to embodiments of the present systems and methods.

In embodiments, the approach may be based on Voice Activity Detector (VAD) systems, implemented with sound pressure level as feature representation and thresholding for the decision making, see above. The samples of the first channel (containing only the counsellor's voice) with a sound pressure level beyond 55 dB are considered as coming from the counsellor and are set to zero in the second channel. The remaining ones should represent the caller's voice. Additionally, the samples below the threshold in the second channel are also set to zero. However, some smoothing and adjustments may be required as the speech signal is mainly composed of bursts, constantly going up and down. The sound pressure level of the first channel has to be below the threshold for a certain time (defined as 3000 samples here) not to be appropriated to the counsellor's. In this manner, the speech signal should not be brutally cut off. FIG. 16 illustrates the results of the voice extraction from a random recording and seems quite efficient. The process is quite simple and easily computed, resulting in fast algorithms, which is a requirement for real-time analysis.

In embodiments, the pre-processing and features extraction may be performed on both the counsellor's and caller's voices, as both are analyzed. The idea is to find the characteristics that will help to estimate the severity of the caller's suicidal impulse but also to evaluate the counsellor's apprehension, how does he perceive the situation.

Figure 17:
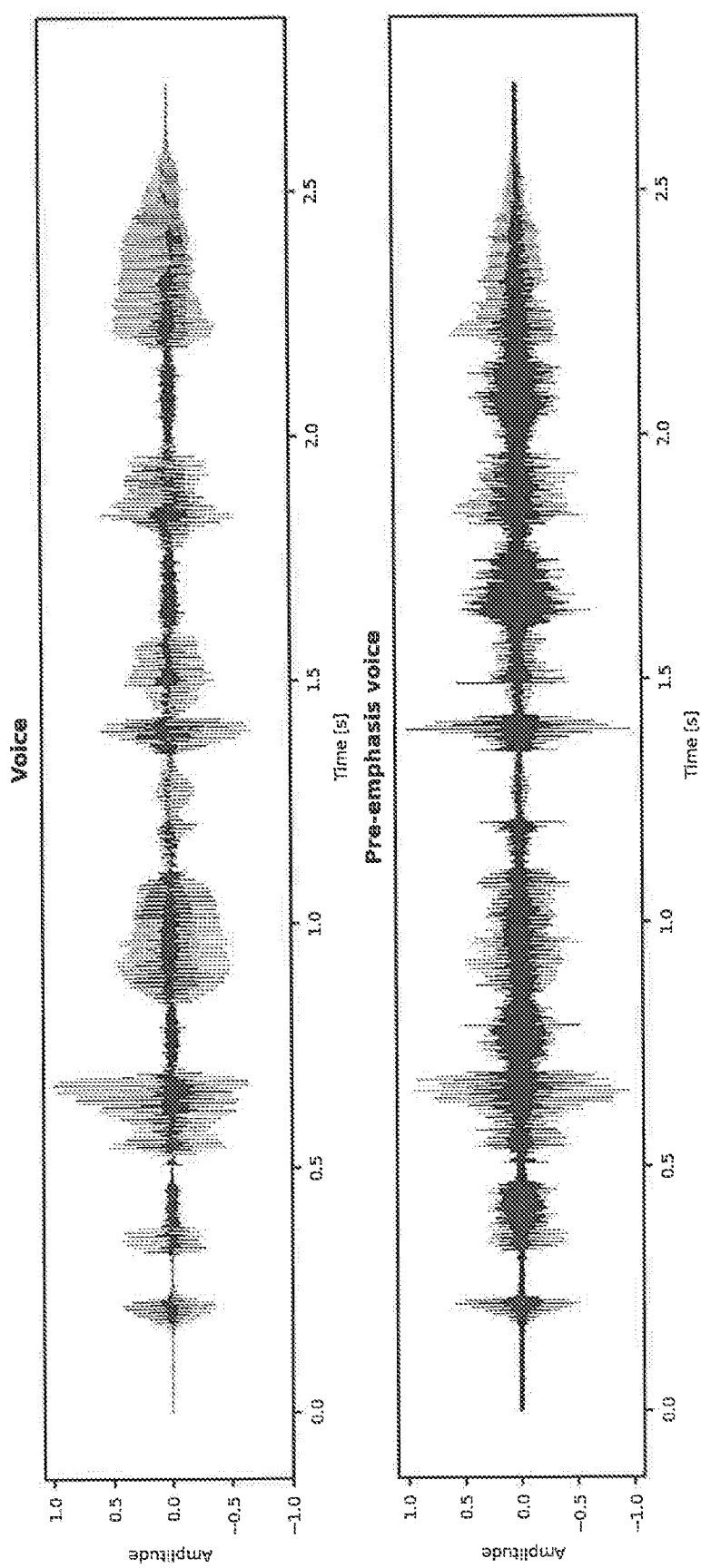
FIG. 17 is an exemplary illustration of pre-emphasis according to embodiments of the present systems and methods.

The last pre-processing step is the pre-emphasis, see above, where a filter is used to boost the high frequency components. FIG. 17 shows the impact of this process on a segment of the recording. This main disadvantage, which might be problematic for the speech analysis, is its increase of the background noise. Embodiments may use a noise reduction algorithm in the pre-processing process.

Short-time analysis. To achieve local stationarity of the speech properties, the signal may be split into overlapping frames and the feature extraction may be performed on each frame. The choice of the frame length and frame period may be determined as described above. A frame of 25 ms with 10 ms between each frame is widely used and embodiments may use such. The signal may be first padded with the necessary amount of zeros to obtain frames having all an equal number of samples independently of the recording duration.

Figure 18:
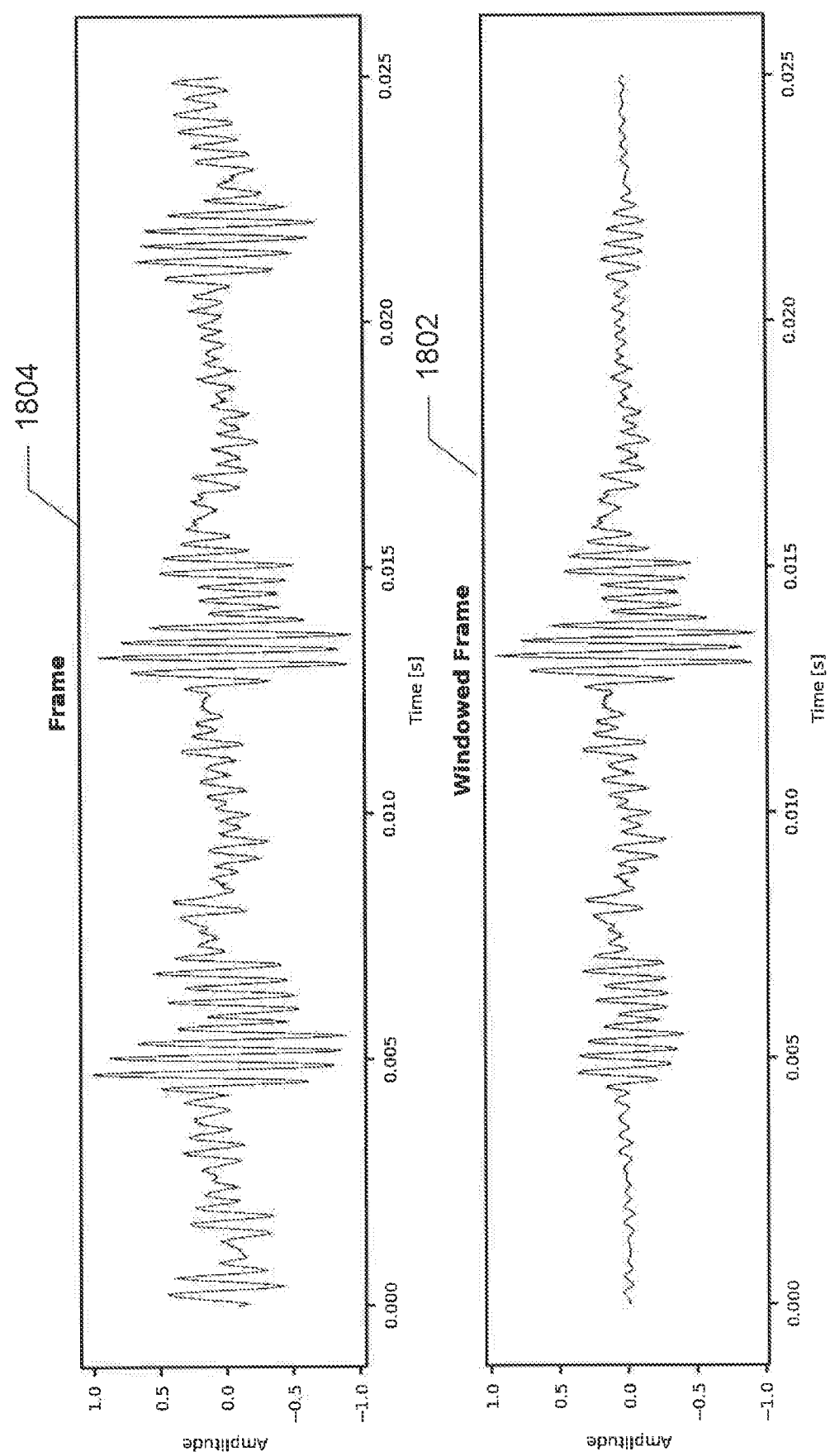
FIG. 18 is an exemplary illustration of application of a Hamming window on a frame according to embodiments of the present systems and methods.

In order to satisfy the Fourier Transform assumptions, a weighting function may be applied to each frame as described above. FIG. 18 illustrates the impact 1802 of a Hamming Window on one frame of the recording (25 ms) 1804. The amplitude attenuation at the edges of the frame are clearly perceptible.

Feature Extraction. The original data contains some redundancies and a large amount of information partially unnecessary for the task to perform here. Before feeding the model, specific feature representations are extracted from the data frames. A feature well appropriate for speech analysis is the Mel Frequency Cepstral Coefficient (MFCC).

MFCC belongs to the category of features working in the frequency domain. The first step in their computation is the transformation of the signal from time to frequency domain. This is achieved by the N-point DFT, which is performed thanks to a Fast Fourier Transform (FFT) algorithm, as described above.

Figure 19:
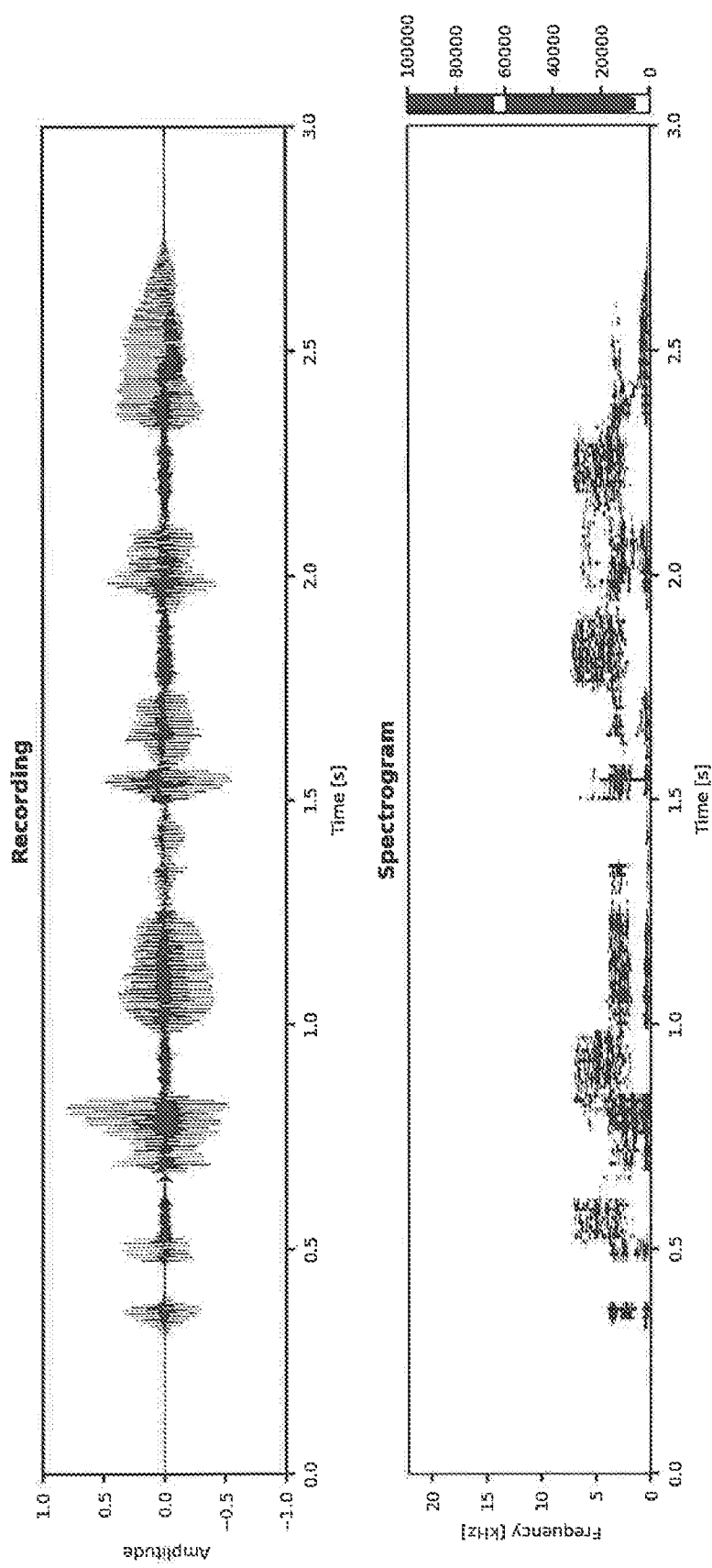
FIG. 19 is an exemplary illustration of a spectrogram of a recording according to embodiments of the present systems and methods.

Only the amplitude of the spectrum is needed and now considered. The spectrogram of 30 seconds of recording is shown in FIG. 19. It allows to visualize how the spectrum of frequencies evolves with time. This spectrogram reveals that the major part of this recording is concentrated in the low frequencies. The overall spectrum is also in the lowest part of the amplitude range, with only a few values of high amplitude. It demonstrates the importance of performing further processing in order to extract only the relevant information.

Figure 20:
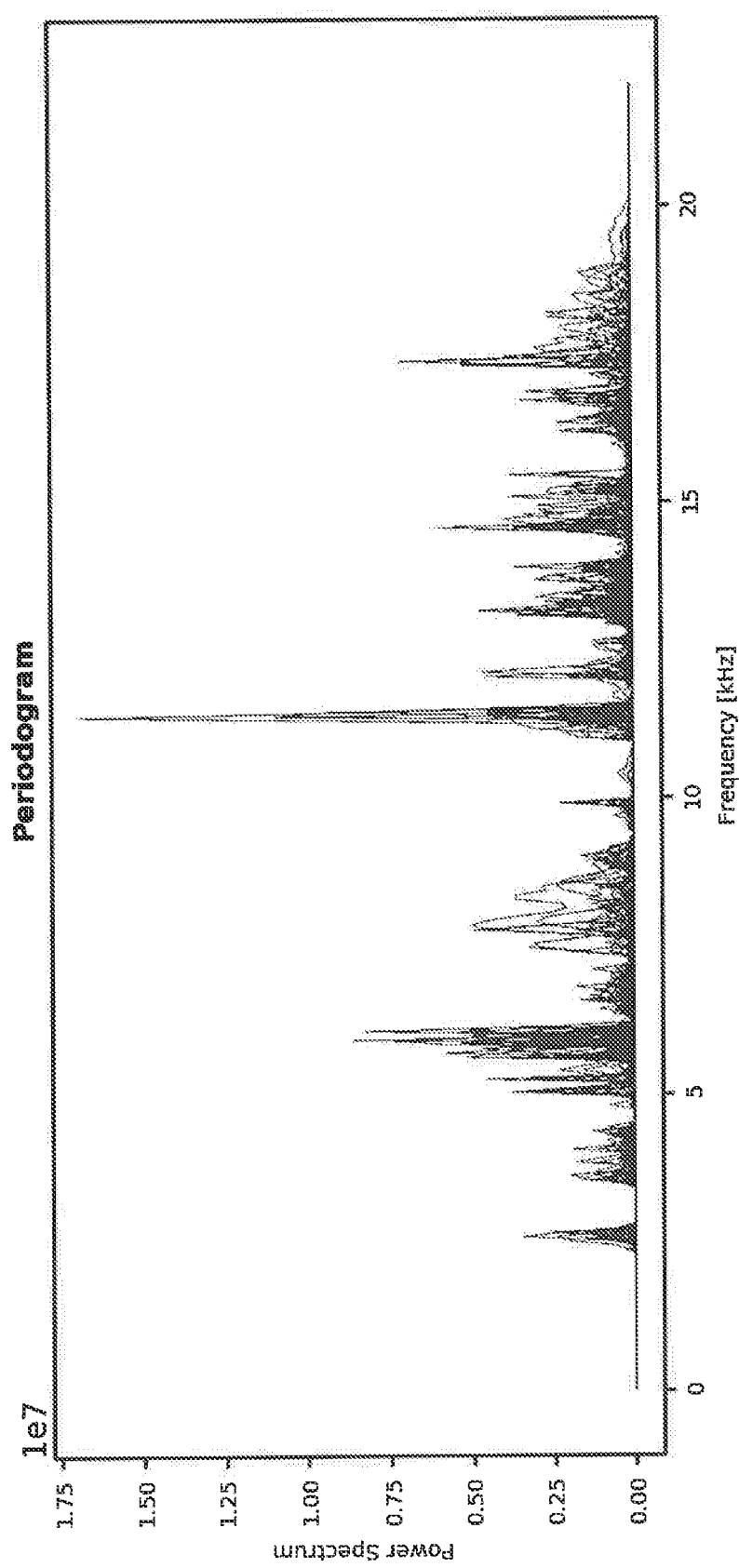
FIG. 20 is an exemplary illustration of a periodogram according to embodiments of the present systems and methods.

The main idea with MFCC is to assess characteristics being a proper representation of the human auditory perception. The power spectrum of the signal is the next logical step. The periodogram plotted in FIG. 20 illustrates an estimation of the signal spectral density. The dominant frequencies of the signal can thus be identified. Here, for instance, the spectrum seems to peak around 11500 Hz.

Figure 21:
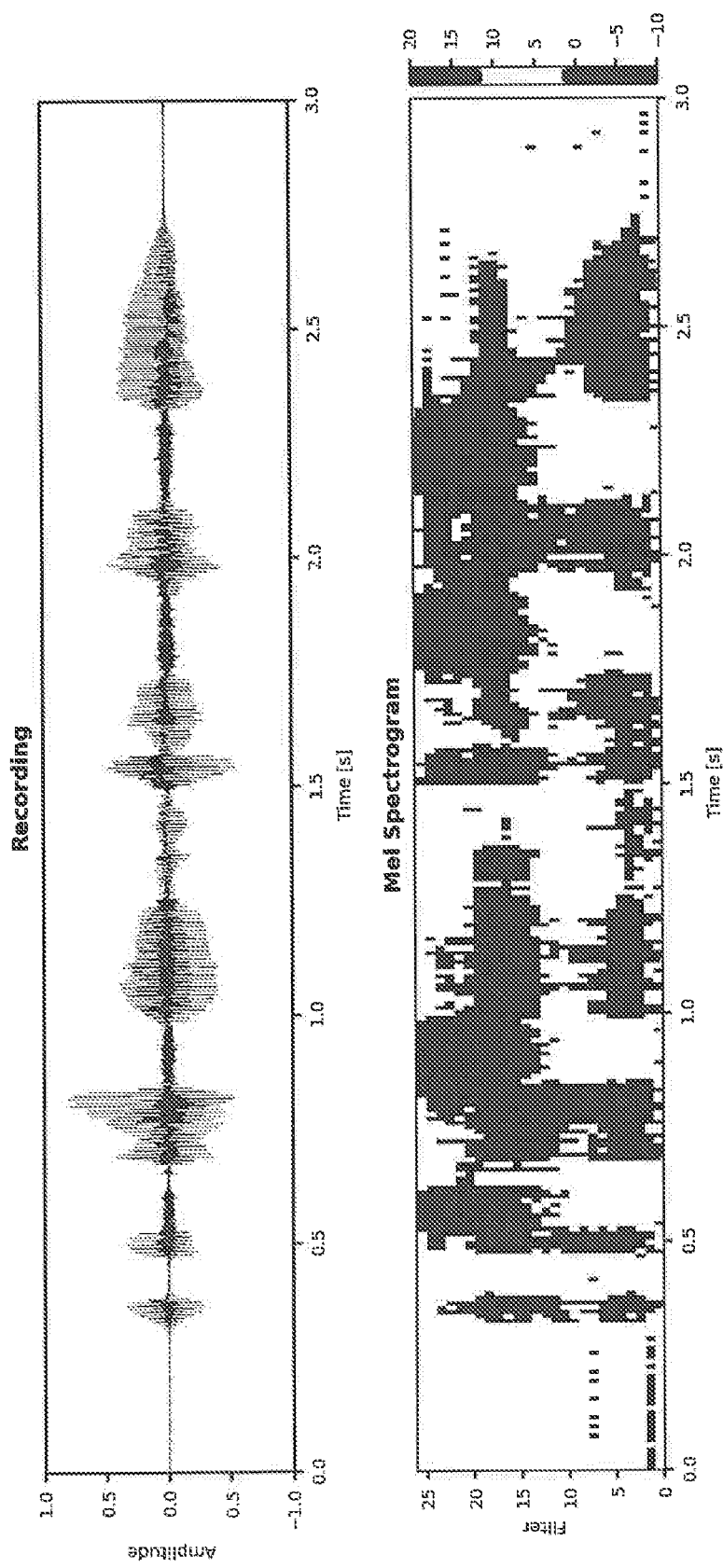
FIG. 21 is an exemplary illustration of a mel spectrogram according to embodiments of the present systems and methods.

To better represent the non-linearity of the human frequency perception, a filter-bank containing, for example, 26 triangular filters with Mel-frequency scaling is applied to the power spectrum. The design and number of filters is described above. FIG. 21 shows the evolution of Mel-filter banks over time. The interpretation of the plot seems facilitated. However, as previously mentioned, those features are highly correlated. The redundancy of the information between filters is clearly visible in FIG. 21.

Figure 22:
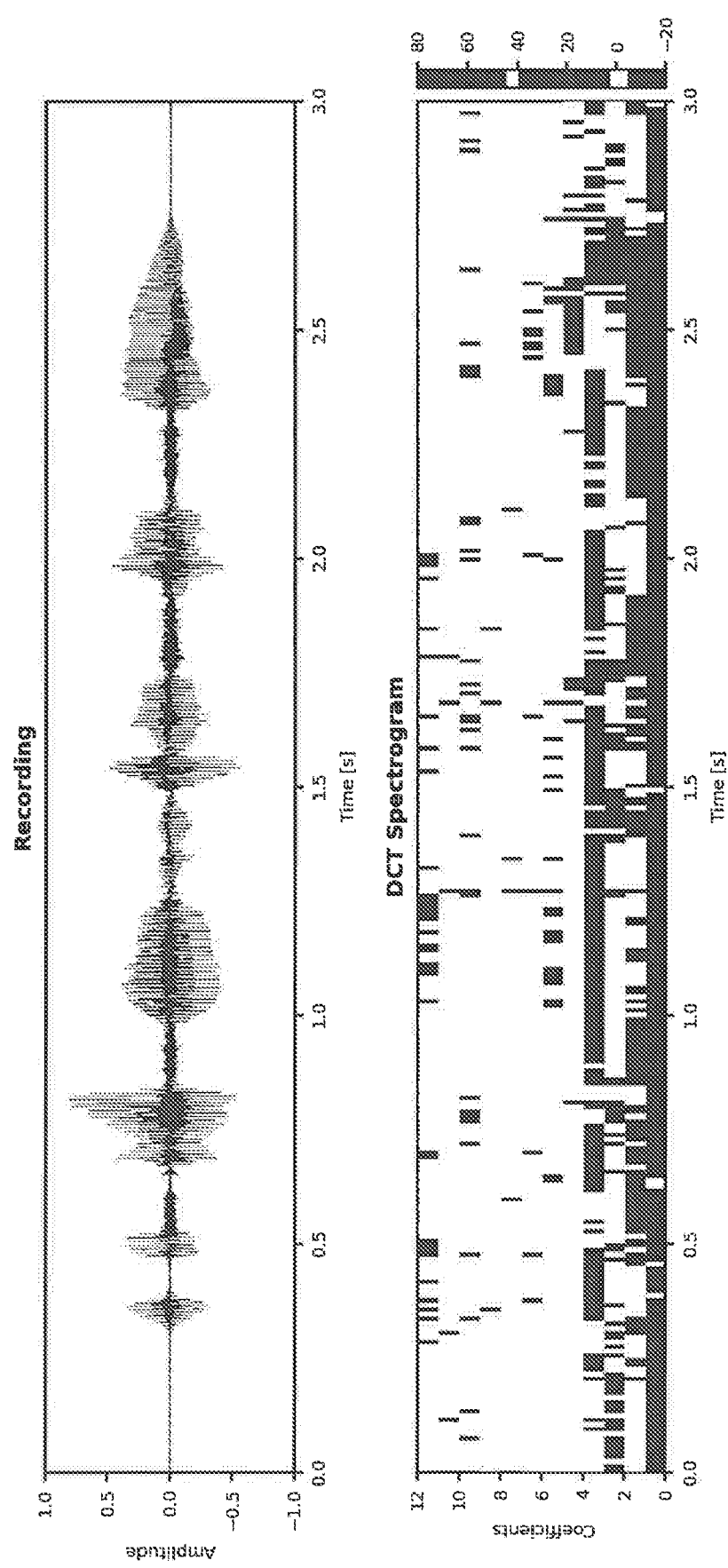
FIG. 22 is an exemplary illustration of a 12 MFCC features spectrogram according to embodiments of the present systems and methods.

The MFCCs are computed from the Mel-filter banks by executing the Discrete Cosine Transform (DCT) as described above. As the information is condensed in the first coefficients, it is not necessary to keep more than the first $12^{th}$ components. Limiting the number of components releases the memory load and increases the computational efficiency. Those 12 coefficients are illustrated over time in FIG. 22. Looking at this plot, the lowest order component seems to be the one carrying the most amount of information. The others only show small fluctuations throughout the recording with also very low amplitude.

Figure 23:
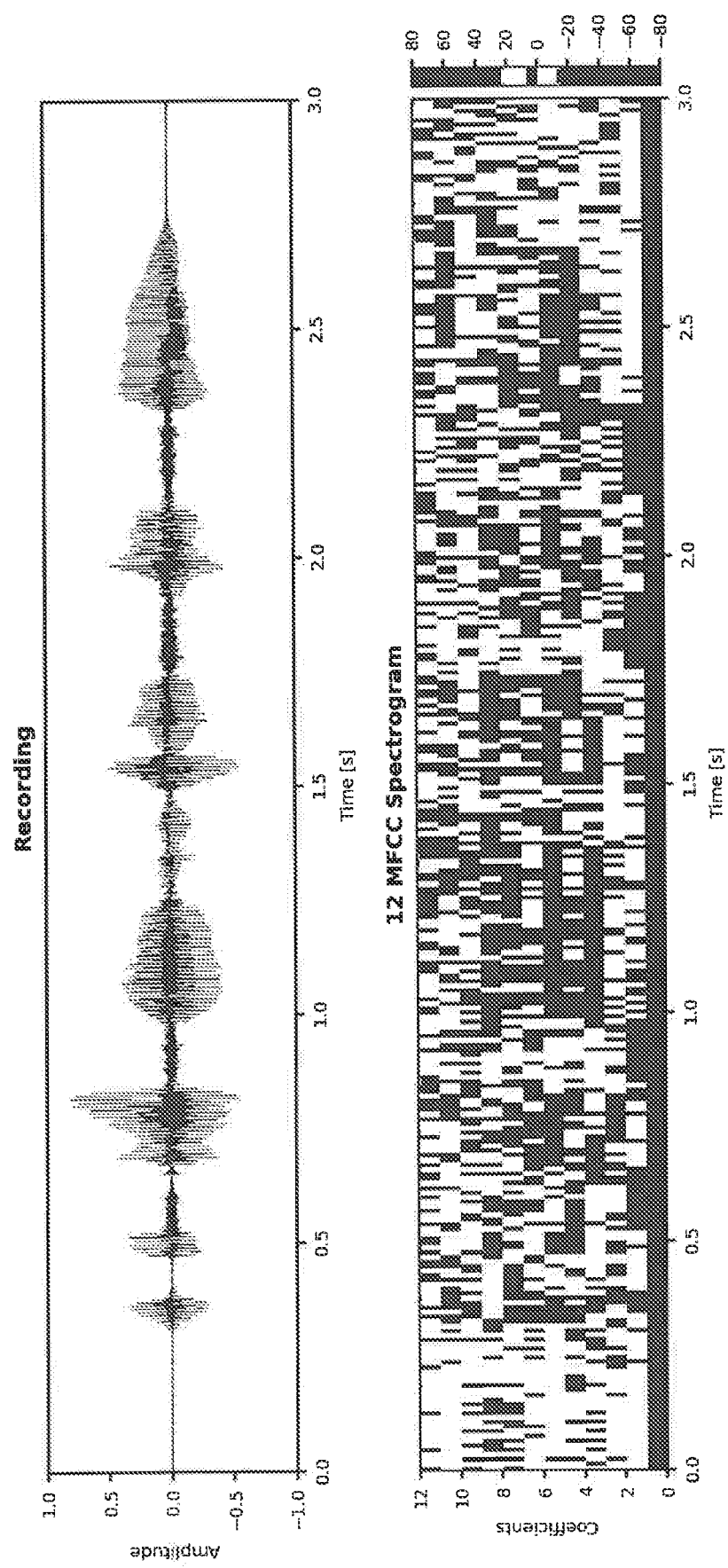
FIG. 23 is an exemplary illustration of a 12 MFCC after littering spectrogram according to embodiments of the present systems and methods.

Sinusoidal liftering is then performed to emphasize the low order components. As described above, this operation enlarges the amplitude of higher components. The results are the widely used features in speech analysis, named MFCCs. Those 12 MFCC after liftering are plotted in a spectrogram in FIG. 23, where the impact of the sinusoidal littering on the high order components is clearly perceptible.

Figure 24:
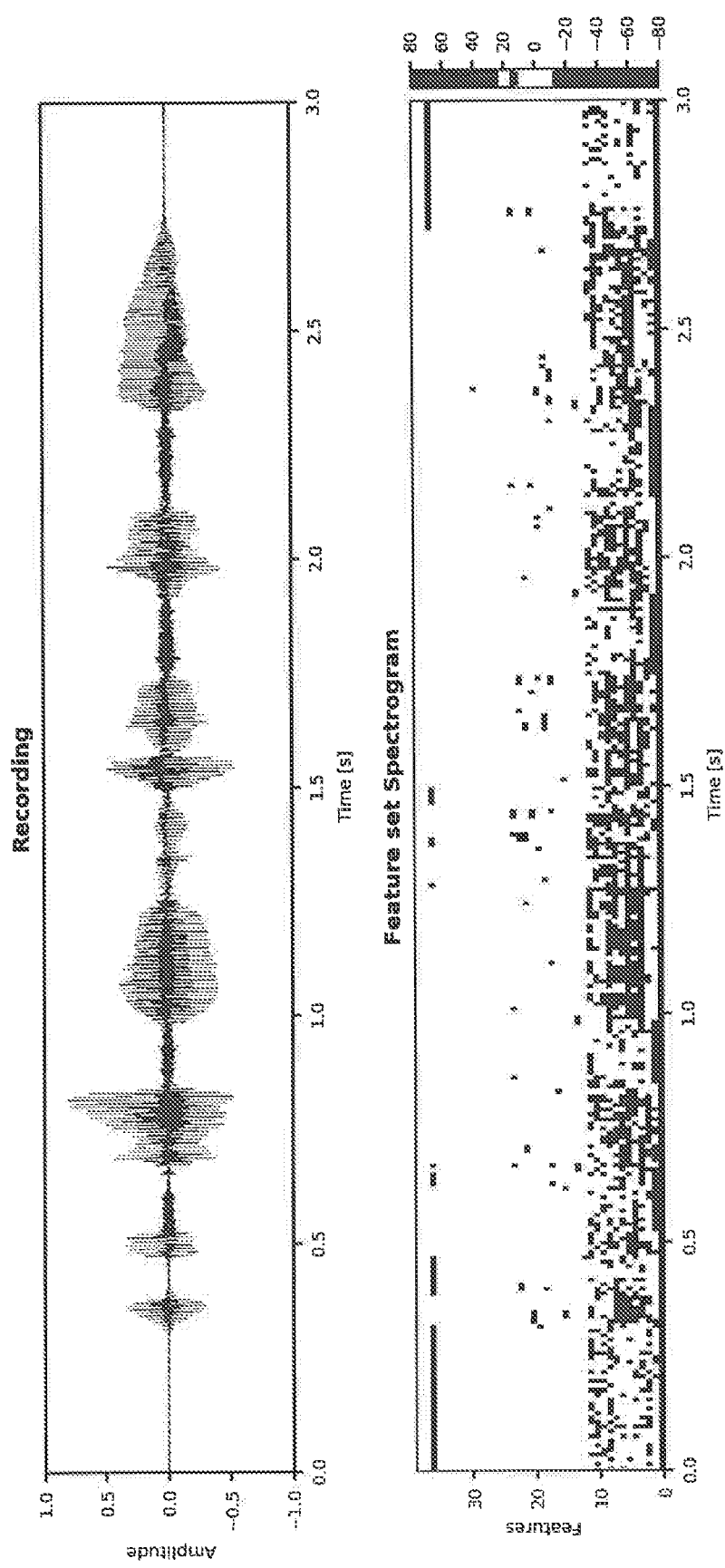
FIG. 24 is an exemplary illustration of a feature set plotted simultaneously as function of time according to embodiments of the present systems and methods.

As the original data is a signal evolving over time, it might also be relevant to see how the MFCCs change throughout the recording. Calculating the delta ($\Delta$) and delta-delta ($\Delta\Delta$) leads to such information. By extending the context of the derivative computation to two frames, the small range changes should become apparent and be revealed. The dynamic of first and second orders of the MFCCs are computed as explained above. The entire feature set is plotted simultaneously as function of time: 12 MFCC+12 $\Delta$+12 $\Delta\Delta$+1 Spectral Energy+1 $\Delta$ Spectral Energy+1 $\Delta\Delta$ Spectral Energy in FIG. 24. In this figure, the 12 first features are the MFCCs. The 12 following correspond to the delta and features 25 to 36 represent the double delta. For this particular recording, only really small fluctuations are perceptible for the first derivative of the MFCCS over time, with amplitude range close to zero. As the acceleration is the derivative of the derivative, small variation in the $\Delta$ results in even less changes in the second derivative. However, it is important to estimate the relevance of the $\Delta$ and $\Delta\Delta$ before including them to the feature set in order to avoid loading the system with unnecessary information.

Finally, three other features are added to the feature set, the spectral energy with its first and second derivatives. As described above, the spectral energy is computed from the power spectrum, already executed for the MFCCs. Reusing previous calculation will greatly reduce the computing load. Those characteristics are also plotted in FIG. 24, being the last three features. The whole feature set implemented in this project is thus represented in this figure. The spectral energy of this recording seems almost constant over time, reason why its first and second derivatives are mostly zeros.

Evaluation. A validation of the feature extraction process may be performed through a simple "voice-to-text" task. The idea is to re-transcribe the content of an audio file using a small BLSTM-RNN, described above, and the designed feature set. It is a frequent speech analysis challenge for which MF CC features are typically used. Even though, widely studied, this task remains challenging. It typically requires a lot of memory and computational power. For this reason, the evaluation work may focus on a small subset of the CSTR VCTK corpus.

Accordingly, the training set for this example may be restricted to the transcribing of 20 recordings. The model validation is assessed on randomly truncated recordings of the training set. Including a validation step is of great importance to ensure that the model is as generalizable as possible. It would have been more relevant and realistic to validate the process on completely new sequences. However, the training set is clearly not big enough to meet all potential English phonemes and the model would probably result in poor outcomes with unseen recording. This should nevertheless prevent a completely naive "voice-to-text" mapping and reveal the potential of the approach.

The model and its parameters for this example are defined as follows. In total, there are 40 epochs, where an epoch represents one training cycle. During each epoch, the model is going through 100 samples randomly selected within the training set, to learn how to perform the transcription from voice to text. The learning coefficients are then quickly evaluated over a validation sample, before starting the next epoch. More particularly, the BLSTM-RNN architecture contains one layer with 128 hidden units. The optimization is performed through the Momentum algorithm, with a learning rate of 0.001 and a momentum coefficient of 0.9. The AdamOptimizer is an improvement of the classical. Stochastic Gradient Descent. It takes into consideration the moving averages of the parameters (momentum), which helps to dynamically adjust the hyperparameters. The whole is performed with a Connectionist Temporal Classification (CTC) loss function, described above.

First, the model is trained multiple times with a diverse feature set extracted with the new implementation. All of the hyperparameters are similar for each run. Keeping them constant throughout the trials should help to define and show the relevance of the selected features. The only difference is basically the number of features. Those results are represented in Table 2. First, only the 12 MFCCs are extracted and used as inputs to the BLSTM-RNN for executing the small ASR task. Then, all the features implemented in this work are used, namely 12 MFCCs, 12 $\Delta$ MFCCs, 12 $\Delta\Delta$ MFCCs and the spectral Energy with its first and second order derivatives, for a total of 39 features. This should indicate and confirm that adding derivatives of MFCCs further improves the model performance.

TABLE 2

| | | | | | | |
|---|---|---|---|---|---|---|
| 12 | 2.100 | 0.000 | 18.880 | 0.095 | 82.714 | 3309.086 |
| 39 | 7.203 | 0.001 | 44.557 | 0.142 | 101.504 | 4060.907 |

Results of the BLSTM-RNN for the "Voice-to-text" Task

Globally, the model is capable of correctly transcribing the set of files presented. As shown in FIG. 25, there are a few mistakes but the result is very encouraging and promising for a first try. The network rapidly learns certain patterns. One is that some characters are more frequent than others, particularly e, a, r, s, t and space. It also quickly learns that the sequence of consonant-vowel-consonant is really common in the English language.

Figure 26:
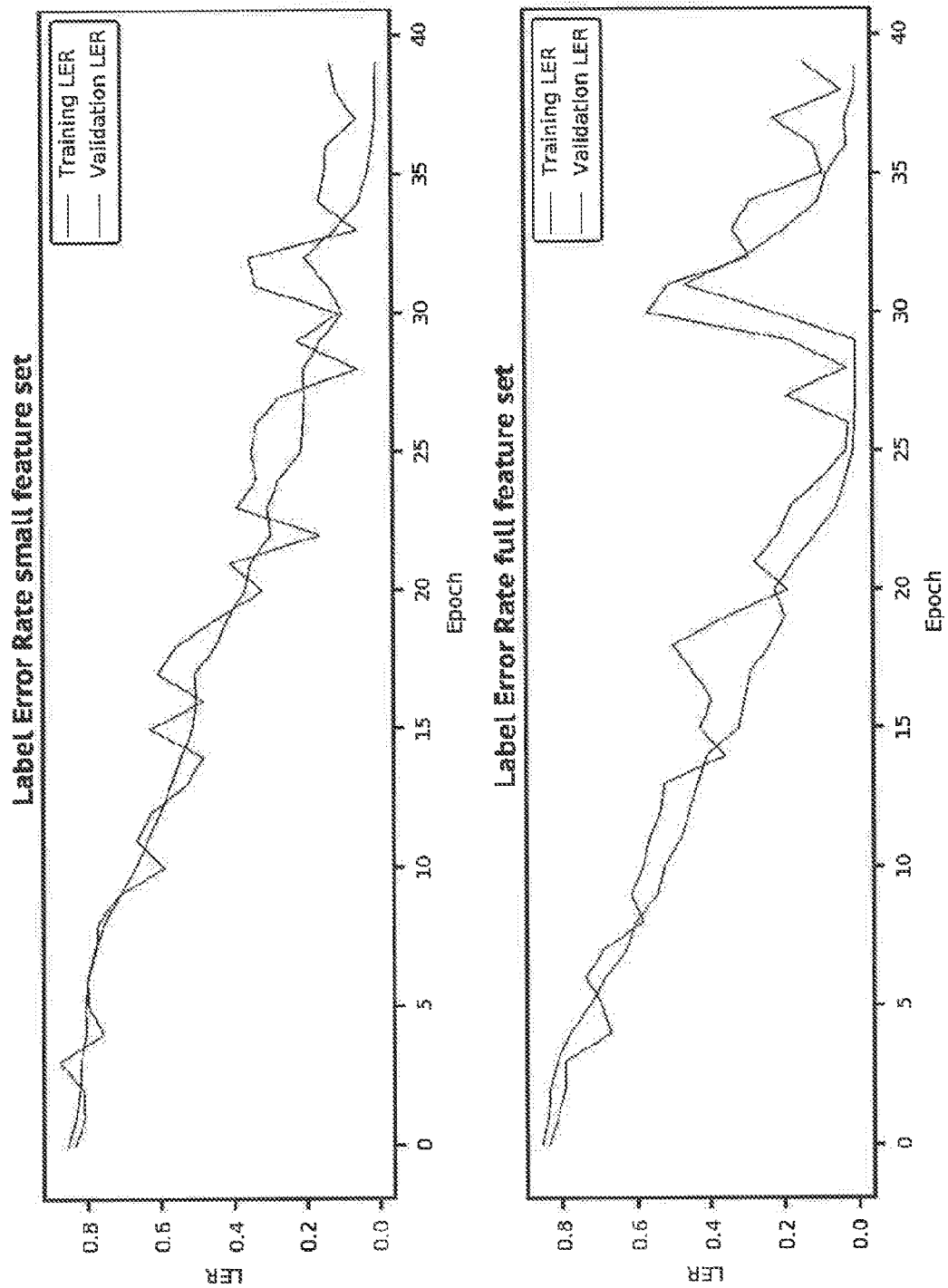
FIG. 26 is an exemplary illustration of a Label Error Rate per epoch for learning according to embodiments of the present systems and methods.

Independently of the feature set, the results in Table 2 also demonstrate this quick learning capability. There are no huge differences discernible between the two feature sets used, except perhaps the validation cost in this particular example. However, it is relevant to remind that the validation is only performed on a single sample and the cost can easily change according to the complexity of this sample. The average time per epoch and thus the total process is a little bit longer with the full version of the feature set, which absolutely makes sense, since more computations are required for the additional feature representations. However, the time difference of the total process remains quite small. Furthermore, comparing the learning curves shown in FIG. 26, the Label Error Rate (LER), described above, used as an accuracy reference, seems to decay faster when more features are considered. This probably means that enlarging the feature set has a positive effect on the learning process and that more particularly the derivatives of the MFCCs and the Spectral energy carry relevant information for speech analysis task.

The results are then compared to those obtained with a similar network and exactly the same hyperparameters, but with a known feature extraction library. For example, the library named python_speech_features provides speech features, such as MFCCs and filter banks, commonly used for ASR. In python_speech_features, the feature extraction is processed in Python. The features are numpy arrays that are given as inputs to the network through a feed director, which provides the data at each epoch. The novelty and particular interest of the features extraction proposed in this project is its direct and complete implementation in TensorFlow.

Figure 27:
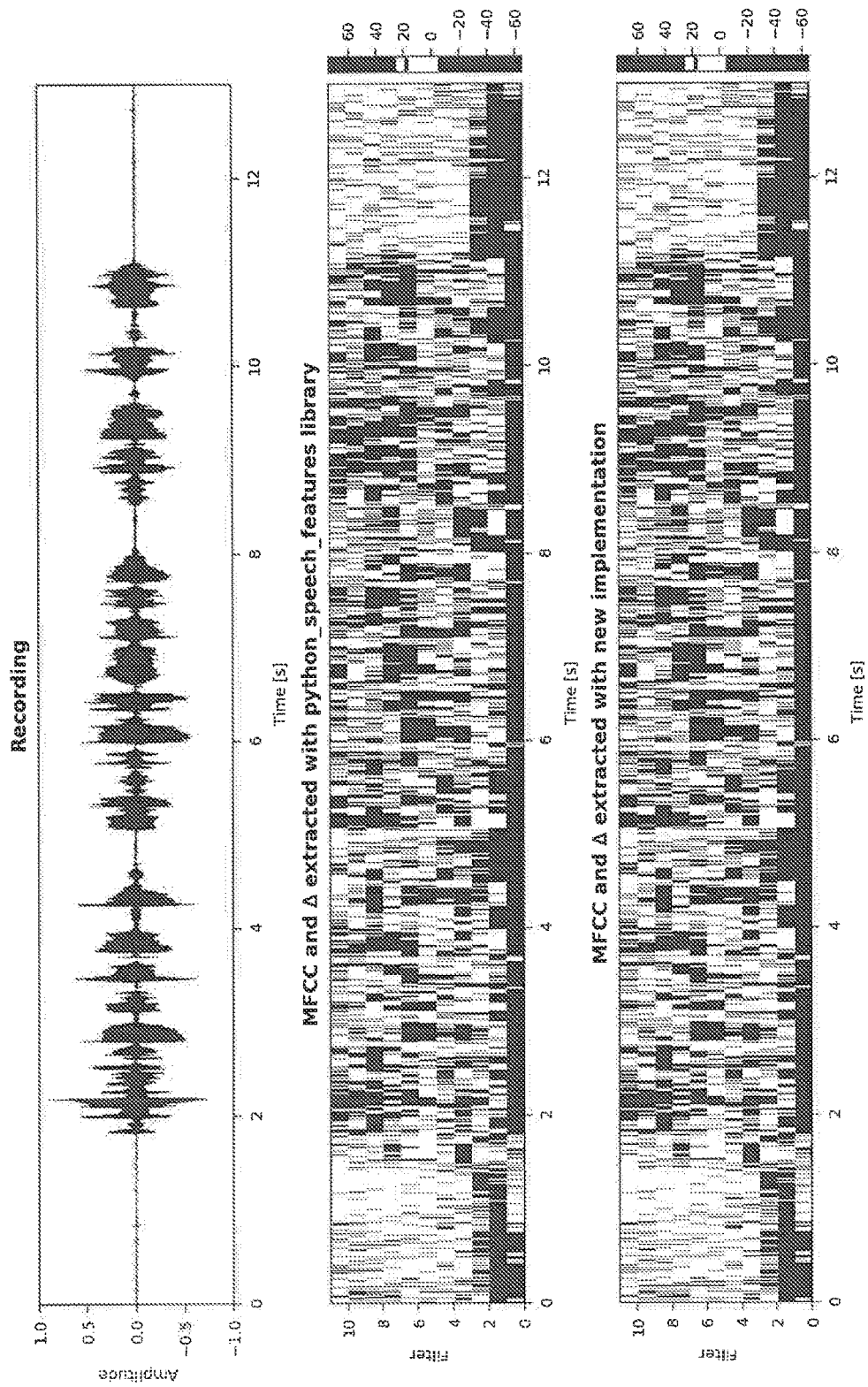
FIG. 27 is an exemplary illustration of a comparison between extraction of 12 MFCCs according to embodiments of the present systems and methods.

FIG. 27 illustrates a comparison between extraction of 12 MFCCs with python_speech_features and new implementation and shows that the MFCCs extracted from a CSTR VCTK recording sample of about 13 seconds with either the python speech features or the new implementation, hut the same parameters, are identical, as expected. This principally demonstrates that the computations of the feature extraction are done properly in the new implementation.

Table 3 represents the results of the small ASR task performed with the two feature extraction implementations. The learning capabilities are quite similar, with both being able to aptly transcribe a sample from the training or validation set. When comparing the computational time required for each implementation, it turns out that it is also equivalent for both implementations. In less than one hour, the model is capable of learning to transcribe the content of 20 speech samples.

TABLE 3

| | | | | | | |
|---|---|---|---|---|---|---|
| Library | 1.479 | 0.000 | 12.996 | 0.035 | 83.407 | 3336.756 |
| New impl. | 2.021 | 0.000 | 18.880 | 0.095 | 82.714 | 3309.086 |

Comparison Between Python_speech_features Library and the New Implementation

Overall, even if the "voice-to-text" task is a bit simplified due to the limited computational power, the results are promising. The new feature extraction implementation is validated by comparing the results obtained with a commonly used feature extraction library. Once again, it demonstrates the potential of the designed acoustic feature set and particularly the MFCCs for typical speech analysis tasks.

Embodiments of the present systems and methods may include improved voice extraction by choosing features other than the sound pressure level and a decision rule other than thresholding. More specific and advanced methods may be implemented. Embodiments may focus on parameter tuning, such as the parameters required for the computation of the MFCCs, including the framing window, the shape and the number of filters for the Mel-filter banks, number of coefficients kept or the littering coefficient. Changes in those values may further improve the performance of the model, making it more suitable for the particular task. MFCCs are not the only well-known acoustics features. In embodiments, other speech characteristics may be utilized for the feature set. For example, pitch is one such feature, which essentially represents the prosody of the speech and the perceived tonality. In embodiments, micro-prosodic; changes descriptors, such as the voice quality may be utilized. The proposed feature set is evaluated through a small ASR task with the CSTR VCTK corpus. Even though the results are promising, the recordings that constitute this database were performed in a controlled environment and under ideal conditions. This is typically not the case of the hotline recordings, which consists of phone calls with background noise and deterioration throughout the system. In embodiments, the recordings may be in an environment that is similar to the application. In embodiments, assessing the accuracy of the extracted features may be done on a corpus that is closer to the hotline call recordings. In embodiments, further pre-processing or additional feature representations may be utilized. For example, one possibility is to use simulated phone signals, such as the NTIMIT corpus, which is a transmission of the well-known TIMIT database through a telephone network. In embodiments, the implemented system, including voice extraction and feature extraction, may be evaluated during actual on-line recording.

In embodiments, three steps of a system for evaluating suicide risk in hotline calls through speech analysis were investigated. The first part was focused on the pre-processing of the audio signal. During the hotline call, the recording device will output a stereo file, that will be used as inputs for the speech analysis. This type of raw signal cannot directly feed the model. In embodiments, the goal of the system is to provide an indication of the caller's crisis severity level and feedback related to the counsellor's apprehension of the situation. Accordingly, each voice may be analyzed separately. In embodiments, an extraction using the principal of phase inversion may be used. In embodiments, the voices may be separated based on the sound pressure level.

Once the counsellor's and caller's voices were extracted, feature extraction may be performed. The Mel Frequency Cepstral Coefficients (MFCCs) are well-known acoustic feature representations, which have proven their efficiency in similar tasks, such as emotion analysis and severity depression estimation. In embodiments, the MFCCs with it first and second order derivatives may be used. In embodiments, spectral energy and its derivatives may be included. In embodiments, multi-threading implementations may provide on-line processing. In embodiments, a multi-threading audio feature extraction library such as openSMILE may be used. In embodiments, the process may be implemented in a programming language, such as C++. In embodiments, the classification module may be implemented using Tensor-Flow. For example, with a feature extraction implemented in TensorFlow, not only the Neural Network can be optimized but also the entire tree. Additionally, TensorFlow allows more flexibility. For instance, each process or computation can be executed either on the CPU or GPU of the computer. Some parameters optimization could also be performed easily in TensorFlow. As mentioned above, in embodiments, parameters such as the ones defining the Mel-filter banks or other coefficients required for the MFCC computation may be optimized for the particular task.

In embodiments, an on-line processing implementation may be used. In embodiments, computing the whole simultaneously as the recording is going on may be performed. In embodiments, the speech analysis may be performed on short sequences of recording. In embodiments, computational algorithms may be of low computational time and complexity, in order to achieve a small time delay between the incoming speech sequence and the output value. In embodiments, the mechanism of Threading and Queues of TensorFlow may be used. This type of architecture allows continual updating of the system as new data are available. The sequence is kept in the memory until being dequeued for further processing. Elements are continuously added and removed from the queue, but the memory load remains constant as the queue has a restricted storage capability. The system is thus never overloaded. With such an implementation, it is possible to load a new short speech sequence as the recording is going on and to achieve feature extraction on the data already present in the memory.

Figure 28:
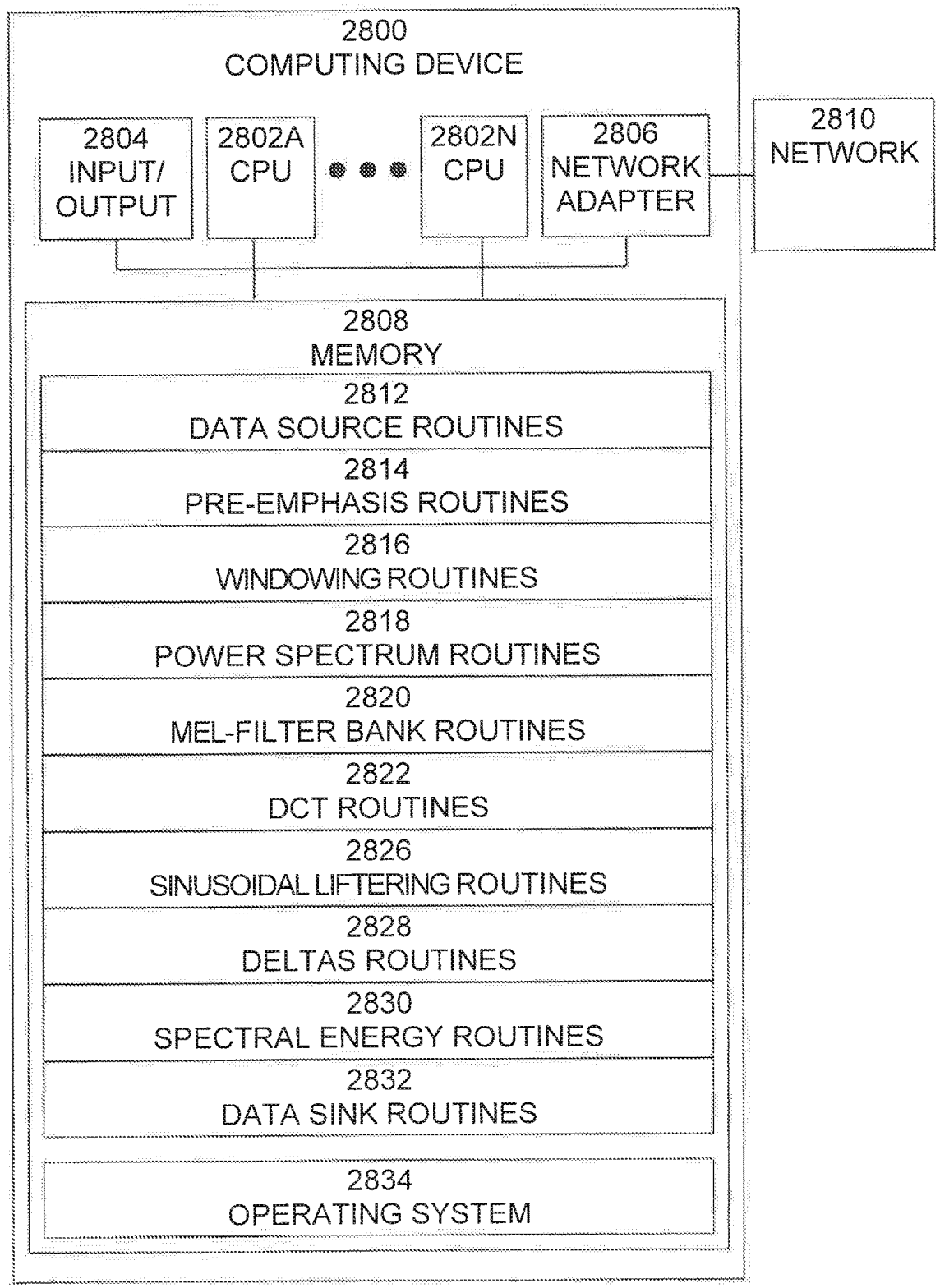
FIG. 28 is an exemplary illustration of a computer system in which embodiments of the present systems and methods may be implemented.

An exemplary block diagram of a computer system 2802, in which processes involved in the embodiments described herein may be implemented, is shown in FIG. 28. Computer system 2802 may be implemented using one or more programmed general-purpose computer systems, such as embedded processors, systems on a chip, personal computers, workstations, server systems, and minicomputers or mainframe computers, or in distributed, networked computing environments. Computer system 2802 may include one or more processors (CPUs) 2802A-2802N, input/output circuitry 2804, network adapter 2806, and memory 2808. CPUs 2802A-2802N execute program instructions in order to carry out the functions of the present communications systems and methods. Typically, CPUs 2802A-2802N are one or more microprocessors, such as an INTEL CORE® processor. FIG. 28 illustrates an embodiment in which computer system 2802 is implemented as a single multi-processor computer system, in which multiple processors 2802A-2802N share system resources, such as memory 2808, input/output circuitry 2804, and network adapter 2806. However, the present communications systems and methods also include embodiments in which computer system 2802 is implemented as a plurality of networked computer systems, which may be single-processor computer systems, multi-processor computer systems, or a mix thereof.

Input/output circuitry 2804 provides the capability to input data to, or output data from, computer system 2802. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 2806 interfaces device 2800 with a network 2810. Network 2810 may be any public or proprietary LAN or WAN, including, but not limited to the Internet.

Memory 2808 stores program instructions that are executed by, and data that are used and processed by, CPU 2802 to perform the functions of computer system 2802. Memory 2808 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (BATA), or a variation or enhancement thereof, or a fiber channel-arbitrated loop (FC-AL) interface.

The contents of memory 2808 may vary depending upon the function that computer system 2802 is programmed to perform. In the example shown in FIG. 28, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present communications systems and methods may include any and all such arrangements.

In the example shown in FIG. 28, memory 2808 may include training data source routines 2812, pre-emphasis routines 2814, windowing routines 2816, power spectrum routines 2818, mel-filter routines 2820, DCT routines 2822, sinusoidal littering routines 2826, deltas routines 2828, spectral energy routines 2830, data sink routines 2832, and operating system 2834. Data source routines 2812 may include software routines to obtain or generate incoming data, such as audio recordings. Pre-emphasis routines 2814 may include software routines to perform pre-emphasis processing. Windowing routines 2816 may include software routines to perform windowing processing. Power spectrum routines 2818 may include software routines to perform power spectrum processing. Mel-filter routines 2820 may include software routines to perform mel-filter processing. DCT routines 2822 may include software routines to perform DCT processing. Sinusoidal liftering routines 2826 may include software routines to perform sinusoidal liftering processing. Deltas routines 2828 may include software routines to perform deltas processing. Spectral energy routines 2830 may include software routines to perform spectral energy processing. Data sink routines 2832 may include software routines to perform data sink processing. Operating system 2834 may provide overall system functionality.

As shown in FIG. 28, the present systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or Hock diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. Those computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the Hock diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A computer-implemented method of determining an emotional or mental state of a person, the method comprising:
   acquiring an audio signal relating to a conversation including the person;
   extracting signal components relating to an emotional or mental state of at least the person by:
      extracting signal features from the audio signal comprising discriminative speech indicators, which differentiate between speech and silence;
      determining which extracted signal features to use; and
      enhancing the robustness of the determination against background noise by adding a hangover time to the extracted signal features in which a label of a current frame of the extracted signal features is kept as speech if a plurality of labels of previous frames of the extracted signal features are identified as speech; and
   outputting information characterizing the extracted emotional or mental state of the person.

2. The method of claim 1, wherein acquiring the audio signal relating to a conversation comprises:
   recording a conversation between a caller to suicide help line and a counselor of the suicide help line.

3. The method of claim 1, wherein:
   determining which extracted signal features to use comprises using at least one of a linear classifier model, a decision tree model, a Gaussian mixture model, a Neural Network model, a thresholding model.

4. The method of claim 3, wherein the at least one model is trained using recordings of conversations wherein the emotional or mental state of the at least one party to the conversation has been previously determined.

5. The method of claim 4, wherein extracting signal features from the audio signal comprises using at least one of: an Energy, Zero-crossing rate method, a linear prediction and pitch estimation method, a Spectral entropy method, a Spectral envelope method, and a Cepstral Coefficient method.

6. The method of claim 4, wherein extracting signal features from the audio signal comprises:
   performing pre-emphasis filtering on the audio signal to generate a pre-emphasis filtered signal;
   performing windowing processing on the pre-emphasis filtered signal to generate a windowed signal;
   performing discrete Fourier transform processing on the windowed signal to form a Fourier transformed signal;
   performing power spectrum processing on the Fourier transformed signal to form a power spectrum signal;
   performing filter bank processing on the power spectrum signal to form a filter bank signal;
   performing logarithm processing on the filter bank signal to form a logarithm signal;
   performing discrete cosine transform processing on the logarithm signal to form a discrete cosine transformed signal;
   performing sinusoidal liftering processing on the discrete cosine transformed signal to form a plurality of Mel-Cepstral coefficients;
   performing discrete energy spectrum processing on the power spectrum signal to form an energy spectrum signal;
   performing logarithm processing on the energy spectrum signal to form an energy coefficient; and
   performing delta processing on the plurality of Mel-Cepstral coefficients and on the energy coefficient to form a plurality of Mel-Cepstral coefficients deltas and double deltas and an energy coefficient delta and double delta.

7. A system for determining an emotional or mental state of a person, the system comprising a processor, memory accessible by the processor, and computer program instructions stored in the memory and executable by the processor to perform:
   acquiring an audio signal relating to a conversation including the person;
   extracting signal components relating to an emotional or mental state of at least the person by:
      extracting signal features from the audio signal comprising discriminative speech indicators, which differentiate between speech and silence;
      determining which extracted signal features to use; and
      enhancing the robustness of the determination against background noise by adding a hangover time to the extracted signal features in which a label of a current frame of the extracted signal features is kept as speech if a plurality of labels of previous frames of the extracted signal features are identified as speech; and
   outputting information characterizing the extracted emotional or mental state of the person.

8. The system of claim 7, wherein acquiring the audio signal relating to a conversation comprises:
   recording a conversation between a caller to suicide help line and a counselor of the suicide help line.

9. The system of claim 7, wherein:
   determining which extracted signal features to use comprises using at least one of a linear classifier model, a decision tree model, a Gaussian mixture model, a Neural Network model, a thresholding model; and enhancing the robustness of the determination comprises using a hysteresis rule.

10. The system of claim 9, wherein the at least one model is trained using recordings of conversations wherein the emotional or mental state of the at least one party to the conversation has been previously determined.

11. The system of claim 10, wherein extracting signal features from the audio signal comprises using at least one of: an Energy, Zero-crossing rate method, a linear prediction and pitch estimation method, a Spectral entropy method, a Spectral envelope method, and a Cepstral Coefficient method.

12. The system of claim 10, wherein extracting signal features from the audio signal comprises:

performing pre-emphasis filtering on the audio signal to generate a pre-emphasis filtered signal;

performing windowing processing on the pre-emphasis filtered signal to generate a windowed signal;

performing discrete Fourier transform processing on the windowed signal to form a Fourier transformed signal;

performing power spectrum processing on the Fourier transformed signal to form a power spectrum signal;

performing filter bank processing on the power spectrum signal to form a filter bank signal;

performing logarithm processing on the filter bank signal to form a logarithm signal;

performing discrete cosine transform processing on the logarithm signal to form a discrete cosine transformed signal;

performing sinusoidal liftering processing on the discrete cosine transformed signal to form a plurality of Mel-Cepstral coefficients;

performing discrete energy spectrum processing on the power spectrum signal to form an energy spectrum signal;

performing logarithm processing on the energy spectrum signal to form an energy coefficient; and performing delta processing on the plurality of Mel-Cepstral coefficients and on the energy coefficient to form a plurality of Mel-Cepstral coefficients deltas and double deltas and an energy coefficient delta and double delta.

13. A computer program product for determining an emotional or mental state of a person, the computer program product comprising a non-transitory computer readable storage having program instructions embodied therewith, the program instructions executable by a computer, to cause the computer to perform a method comprising:

acquiring an audio signal relating to a conversation including the person;

extracting signal components relating to an emotional or mental state of at least the person by:

extracting signal features from the audio signal comprising discriminative speech indicators, which differentiate between speech and silence;

determining which extracted signal features to use; and enhancing the robustness of the determination against background noise by adding a hangover time to the extracted signal features in which a label of a current frame of the extracted signal features is kept as speech if a plurality of labels of previous frames of the extracted signal features are identified as speech; and outputting information characterizing the extracted emotional or mental state of the person.

14. The computer program product of claim 13, wherein acquiring the audio signal relating to a conversation comprises:

recording a conversation between a caller to suicide help line and a counselor of the suicide help line.

15. The computer program product of claim 13, wherein:

determining which extracted signal features to use comprises using at least one of a linear classifier model, a decision tree model, a Gaussian mixture model, a Neural Network model, a thresholding model; and enhancing the robustness of the determination comprises using a hysteresis rule.

16. The computer program product of claim 15, wherein the at least one model is trained using recordings of conversations wherein the emotional or mental state of the at least one party to the conversation has been previously determined.

17. The computer program product of claim 16, wherein extracting signal features from the audio signal comprises using at least one of: an Energy, Zero-crossing rate method, a linear prediction and pitch estimation method, a Spectral entropy method, a Spectral envelope method, and a Cepstral Coefficient method.

18. The computer program product of claim 16, wherein extracting signal features from the audio signal comprises:

performing pre-emphasis filtering on the audio signal to generate a pre-emphasis filtered signal;

performing windowing processing on the pre-emphasis filtered signal to generate a windowed signal;

performing discrete Fourier transform processing on the windowed signal to form a Fourier transformed signal;

performing power spectrum processing on the Fourier transformed signal to form a power spectrum signal;

performing filter bank processing on the power spectrum signal to form a filter bank signal;

performing logarithm processing on the filter bank signal to form a logarithm signal;

performing discrete cosine transform processing on the logarithm signal to form a discrete cosine transformed signal;

performing sinusoidal liftering processing on the discrete cosine transformed signal to form a plurality of Mel-Cepstral coefficients;

performing discrete energy spectrum processing on the power spectrum signal to form an energy spectrum signal;

performing logarithm processing on the energy spectrum signal to form an energy coefficient; and performing delta processing on the plurality of Mel-Cepstral coefficients and on the energy coefficient to form a plurality of Mel-Cepstral coefficients deltas and double deltas and an energy coefficient delta and double delta.

* * * * *